United States Patent [19]
Wiley et al.

[11] Patent Number: 6,073,085
[45] Date of Patent: Jun. 6, 2000

[54] SYSTEM FOR AUTOMATICALLY TESTING AN ELECTRONIC DEVICE DURING QUIESCENT PERIODS

[75] Inventors: Robert A. Wiley, Tukwila; Abraham H. Kou, Redmond; D. Craig Edwards, Bellevue, all of Wash.

[73] Assignee: Physio-Control Manufacturing Corporation

[21] Appl. No.: 08/755,968

[22] Filed: Nov. 25, 1996

Related U.S. Application Data

[63] Continuation of application No. 08/209,948, Mar. 11, 1994, Pat. No. 5,579,234.

[51] Int. Cl.[7] .............................. G01R 15/12; A61N 1/39
[52] U.S. Cl. .............................. 702/118; 364/489; 371/3; 371/20.1
[58] Field of Search ............................ 702/118; 364/480, 364/481, 489; 371/3, 20.1; 607/142, 5, 4, 8, 26; 600/536; 711/106

[56] References Cited

U.S. PATENT DOCUMENTS

| | | | |
|---|---|---|---|
| 4,164,946 | 8/1979 | Langer | 607/27 |
| 4,488,555 | 12/1984 | Imran | 607/29 |
| 4,619,265 | 10/1986 | Morgan et al. | 607/6 |
| 4,631,701 | 12/1986 | Kappeler et al. | 711/106 |
| 5,020,541 | 6/1991 | Marriott | 600/536 |
| 5,078,134 | 1/1992 | Heilman et al. | 607/4 |
| 5,097,830 | 3/1992 | Eikefjord et al. | 607/8 |
| 5,231,987 | 8/1993 | Robson . | |
| 5,249,573 | 10/1993 | Fincke et al. | 607/6 |
| 5,431,684 | 7/1995 | Archer et al. | 607/5 |
| 5,431,692 | 7/1995 | Hansen et al. | 607/28 |
| 5,453,992 | 9/1995 | Whetsel | 371/22.35 |
| 5,477,858 | 12/1995 | Norris et al. | 600/441 |
| 5,483,165 | 1/1996 | Cameron et al. | 324/427 |
| 5,591,213 | 1/1997 | Morgan | 607/5 |

FOREIGN PATENT DOCUMENTS

WO 94/27674   12/1994   WIPO .

OTHER PUBLICATIONS

VIVALink™AED Semi–Automatic External Defibrillator Users' Manual, © SurVivaLink Corporation, Jan. 1995.

Kasouf, George, "*LCC Versus Confidence Testing During Long–Term Storage*," Annual Reliability and Maintainability Symposium Proceedings, Jan. 27–29, 1981, Philadelphia, Pennsylvania.

Yip, H.T. et al., "*Reliability Evaluation of Protection Devices in Electrical Power Systems*," Reliability Engineering, vol. 9, pp. 191–219, 1984.

(List continued on next page.)

*Primary Examiner*—James P. Trammell
*Assistant Examiner*—Demetra R. Smith
*Attorney, Agent, or Firm*—Christensen O'Connor Johnson & Kindness PLLC

[57] ABSTRACT

A portable electronic unit, such as a defibrillator, includes an autotest system for automatically self-testing various electrical components within the unit during quiescent periods. The autotest system includes an autotest routine that performs an extensive array of rigorous yet time-consuming tests that are impractical to perform during normal modes of operation of the unit. A real-time clock can be set to initiate the autotest routine at a time when the unit is unlikely to be used for its normal mode of operation. The autotest system provides a strip chart printout of the results of the various self-tests performed on the unit, and provides messages on a visual display of any error conditions. If the autotest system detects a needs service malfunction, the operator must acknowledge the error with an input to the unit before the unit will enter into its normal mode of operation. If the autotest system detects a service mandatory malfunction, the unit will discontinue any normal mode of operation until the malfunction is corrected. The autorest system immediately discontinues the autorest routine upon power-up of the unit by an operator for use of the unit in its normal mode of operation.

30 Claims, 15 Drawing Sheets

OTHER PUBLICATIONS

Krause Jr., George S., "*Microprocessing to Reduce MTTR of Analog Systems*," Annual Reliability and Maintainability Symposium Proceedings, Jan. 24–26, 1984, San Francisco, California.

Ramirez, Miguel A., "*Built–In–Test Self–Verification*," Annual Reliability and Maintainability Symposium Proceedings, Jan. 24–26, 1984, San Francisco, California.

Smoot, Sterling, "*Designing Built–In Test for Microprocessors*," Annual Reliability and Maintainability Symposium Proceedings, Jan. 24–26, 1984, San Francisco, California.

Richards, D. W. et al., "*SMART BIT: An AI Approach to Better Systems–Level Built–In Test*," Annual Reliability and Maintainability Symposium Proceedings, Jan. 27–29, 1987, Philadelphia, Pennsylvania.

Buswell, S.M. et al., "*Self–Test of Timing and Control Circuitry*," Annual Reliability and Maintainability Symposium Proceedings, Jan. 26–28, 1988, Los Angeles, California.

Doskocil, Douglas C., "*A Comprehensive Strategy for Implementing BIT*," IEEE International Automatic Testing Conference, Oct. 4–6, 1988, Minneapolis, Minnesota.

Gillespie, D. W. et al., "*BIT & Testability for Millimeter Wave Systems*," IEEE International Automatic Testing Conference, Sep. 25–28, 1989, Philadelphia, Pennsylvania.

Daugherty, G. et al., "*BIT Blueprint Toward More Effective Built in Test*," Annual Reliability and Maintainability Symposium Proceedings, Jan. 23–25, 1990, Los Angeles, California.

Luthra, Puran, "*BIT Analysis: How to Approach it*," Annual Reliability and Maintainability Symposium Proceedings, Jan. 23–25, 1990, Los Angeles, California.

Rosin, A. et al., "*An Approach to the Selection of Built–In–Test Devices*," Annual Reliability and Maintainability Symposium Proceedings, Jan. 23–25, 1990, Los Angeles, California.

"*Background Diagnostics in a Diskette Machine*," IBM Technical Disclosure Bulletin, vol. 30, No. 1, Jun. 1987, Armonk, NY, USA; pp. 300–303, XP002034581.

SYSTEM FOR AUTOMATICALLY TESTING AN ELECTRONIC DEVICE DURING QUIESCENT PERIODS

This appln is a con of 08/209,948 filed Mar. 11, 1994, now U.S. Pat. No. 5,579,234.

TECHNICAL FIELD

This invention relates to electronic self-testing systems, particularly self-testing systems for emergency electronic equipment.

BACKGROUND OF THE INVENTION

With simple electronic devices having only a few functions, a user readily knows when the device malfunctions, e.g., a broken switch fails to provide the expected input when actuated. With complex electronic devices having various functions, however, a user may not be able to determine if a particular function is malfunctioning until the user attempts to execute that function. For example, a user will not known that a disk drive on his or her computer is malfunctioning until the computer performs a read/write function from/to the disk drive.

Several electronic devices currently available provide automatic self-testing upon power-up of the device. For example, a typical personal computer ("PC") performs a power-on self-test, or "POST," each time the PC is powered up. The POST detects errors in the display monitor, the keyboard, the memory, and other basic components within the PC, and produces one or more error messages on the display (or a series of beeps if the display is malfunctioning). A single beep combined with a display of the normal prompt on the display indicate that all components have passed the POST.

Simple and quickly executable self-tests are performed for most complex electronic devices. For example, in the PC, the POST checks the random access memory ("RAM") by simply writing data to each memory location in RAM or series of memory locations, and then reading the data back and comparing it to the data initially written to the memory location. More sophisticated, and accurate, memory tests may be performed. The "walking pattern test" is a known RAM test that writes a value to all of the memory locations in RAM and then writes a new value to only one memory location. All memory locations are then read to determine if the value in the one memory location equals the new value written thereto, and to determine if all the other memory locations have been changed by the writing of the new value to the one memory location. This test continues for each memory location by writing the new value thereto and then reading the values in all memory locations. This test requires a considerable amount of computer processing time. For example, the walking pattern test takes two to three minutes to test 130,000 bytes of RAM. As a result, the walking pattern test is not performed during most RAM self-tests such as the POST. Similarly, while a cyclic redundancy check ("CRC") is known in the art to be a more accurate but time-consuming method of testing read only memory ("ROM"), a quick checksum test is performed instead during most self-tests such as the POST.

With emergency electrical equipment, self-testing before an emergency is important to insure that the equipment is functioning properly and reliably. The emergency equipment, however, must also be available for immediate use. Lengthy self-tests of the emergency equipment prohibit the equipment from being used for its intended purpose while the tests are being performed. Delaying treatment to perform extensive self-tests could threaten a victim's health. Therefore, extensive and lengthy self-tests are impractical for emergency electronic equipment. Most the components in the equipment that require time-consuming tests to insure their proper functioning are simply not tested during power-up of the equipment.

For example, portable defibrillator units currently available only perform the simple read/write tests of the RAM described above and checksum tests of the ROM; extensive tests of the defibrillating components are not performed. These critical components, which provide an electric charge to a patient, are tested only during manufacturing of the defibrillator unit. An operator of the defibrillator unit must therefore submit the unit to regular testing by a skilled technician to ensure that the component not subjected to a self-test are operating properly. These regularly scheduled maintenance periods require downtime for the unit, even if the unit is functioning properly.

Overall, the inventors are unaware of a portable emergency electronic device which provides time-consuming yet thorough tests of its own component while still allowing the device to be readily available in the event of an emergency.

SUMMARY OF THE INVENTION

According to principles of the present invention, a portable electronic unit, such as a defibrillator, includes an autotest system for automatically self-testing the various electrical components within the unit during quiescent periods. The autotest system includes an automatic power-on circuit within the unit that automatically initiates autotest routines at a selected time. The autotest system provides feedback to an operator following the autotest routines, including messages displayed on a display screen and printed on a report. These messages provides proof to the operator that the tests were on a report. These messages provide proof to the operator that the tests were performed, and warn the operator in a timely manner if an error is detected.

In a broad sense, the present invention embodies a method of testing a plurality of circuits in an electronic system comprising the steps of: (1) determining if at least a first circuit in the electronic system is in a quiescent mode of operation; (2) testing an operation of the first circuit if the electronic system is in the quiescent mode of operation, the testing of the first circuit being impractical during a non-quiescent mode of operation of the first circuit; and (3) providing a first indication of an operator of the electronic system if the tested operation of the first circuit is unacceptable. The method further preferably includes the steps of (4) monitoring whether the electronic system enters into a power-up mode, and (5) halting the step if the electronic system enters into the power-up mode.

The step of determining if at least the first circuit in the electronic system is in the quiescent mode of operation includes the steps of: (i) counting at selected intervals; (ii) determining if a count is equal to a predetermined value; (iii) determining whether the electronic system is in a power-down mode if the count is equal to the predetermined value; and (iv) determining that the first circuit in the electronic system is in the quiescent mode of operation if the electronic system is in the power-down mode. The step of determining if at least the first circuit in the electronic system is in the quiescent mode of operation also includes the steps of: (v) determining if the electronic system is in a battery charging mode of operation; and (vi) determining that the first circuit in the electronic system is in the quiescent mode of operation if the electronic system is in the battery charging mode.

The present invention includes an apparatus for testing a plurality of circuits in an electronic system including at least a first circuit having an active mode of operation and a quiescent mode of operation. The electronic system includes a processor circuit coupled to the first circuit for (1) determining whether the first circuit is in the quiescent mode of operation (2) testing the first circuit if the first circuit is in the quiescent mode of operation, (3) outputting a first test result signal indicating a result of the testing, and (4) halting testing of the first circuit if the first circuit is in the active mode of operation. The electronic system also includes an indication circuit coupled to the processor circuit. The indicative circuit output a first indication to an operator in response to the first test result signal.

The present invention further includes a method of testing a defibrillator circuit having an ECG preamplifier, an impedance circuit, and an analog-to-digital converter. The method of testing the defibrillator circuit includes the steps of: (1) providing a voltage pulse signal to an input of the ECG preamplifier, (2) analyzing a first ECG output signal produced by the ECG preamplifier in response to the voltage pulse signal, (3) determining if the first ECG output signal is acceptable, (4) providing a known impedance signal to an input of the impedance circuit, (5) analyzing a first impedance output signal produced by the impedance circuit in response to the impedance signal, (6) determining if the first impedance output signal is acceptable, and (7) providing a first indication to an operator if any of the determining steps are unacceptable.

The method of testing the defibrillator circuit also includes the steps of: (8) providing a first voltage signal to the input of the ECG preamplifier and the impedance circuit, (9) analyzing a second ECG output signal produced by the ECG preamplifier and a second impedance output signal produced by the impedance circuit both in response to the first voltage signal, (10) determining if the second ECG output signal and the second impedance output signal are acceptable, and (11) providing a second indication to the operator if at least one of the second ECG output signal and the second impedance output signal are unacceptable.

The method of testing the defibrillator circuit further includes the steps of: (12) providing a second voltage signal to an input of the analog-to-digital converter, (13) analyzing a first converter output signal produced by the analog-to-digital converter in response to the second voltage signal, (14) determining if the first converter output signal is acceptable, (15) providing a third voltage signal to the input of the analog-to-digital converter. (16) analyzing a second converter output signal produced by the analog-to-digital converter in response to the third voltage signal, (17) determining if the second converter output signal is acceptable, and (18) providing a third indication to the operator if one of the first and second converter output signals is unacceptable.

The present invention solves problems inherent in the prior art by providing a system for automatically testing a portable emergency electronic device during quiescent periods using time-consuming tests, while allowing the device to be readily available in the event of an emergency. Other features and advantages of the present invention will become apparent from studying the following detailed description of the present preferred embodiment, together with the following drawings.

DETAILED DESCRIPTION OF THE PRESENTLY PREFERRED EMBODIMENT

Figure 1A:
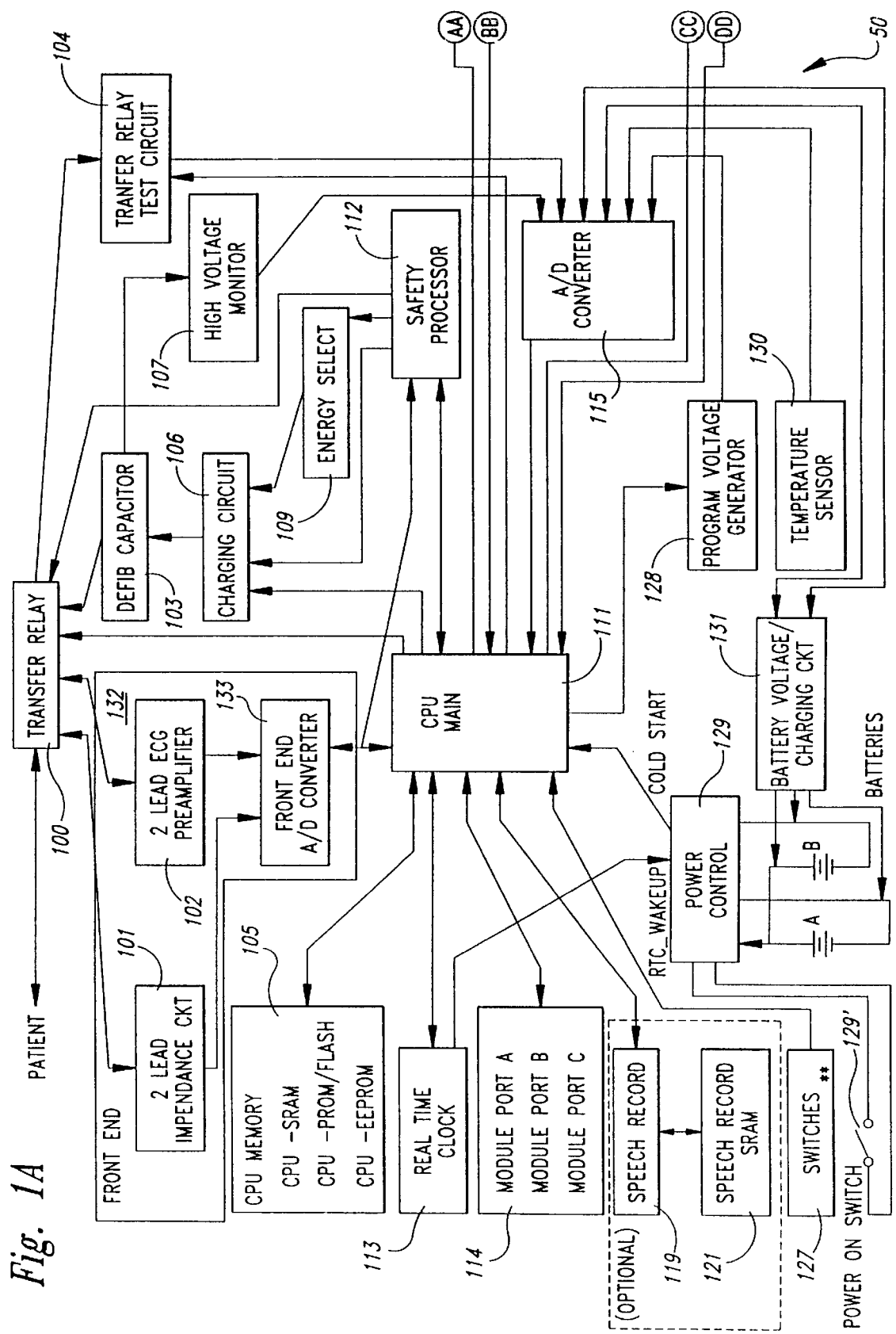
FIGS. 1A and 1B are block diagram of a defibrillator unit having an autotest system for automatically testing the unit during quiescent periods under the present invention.
Figure 1B:
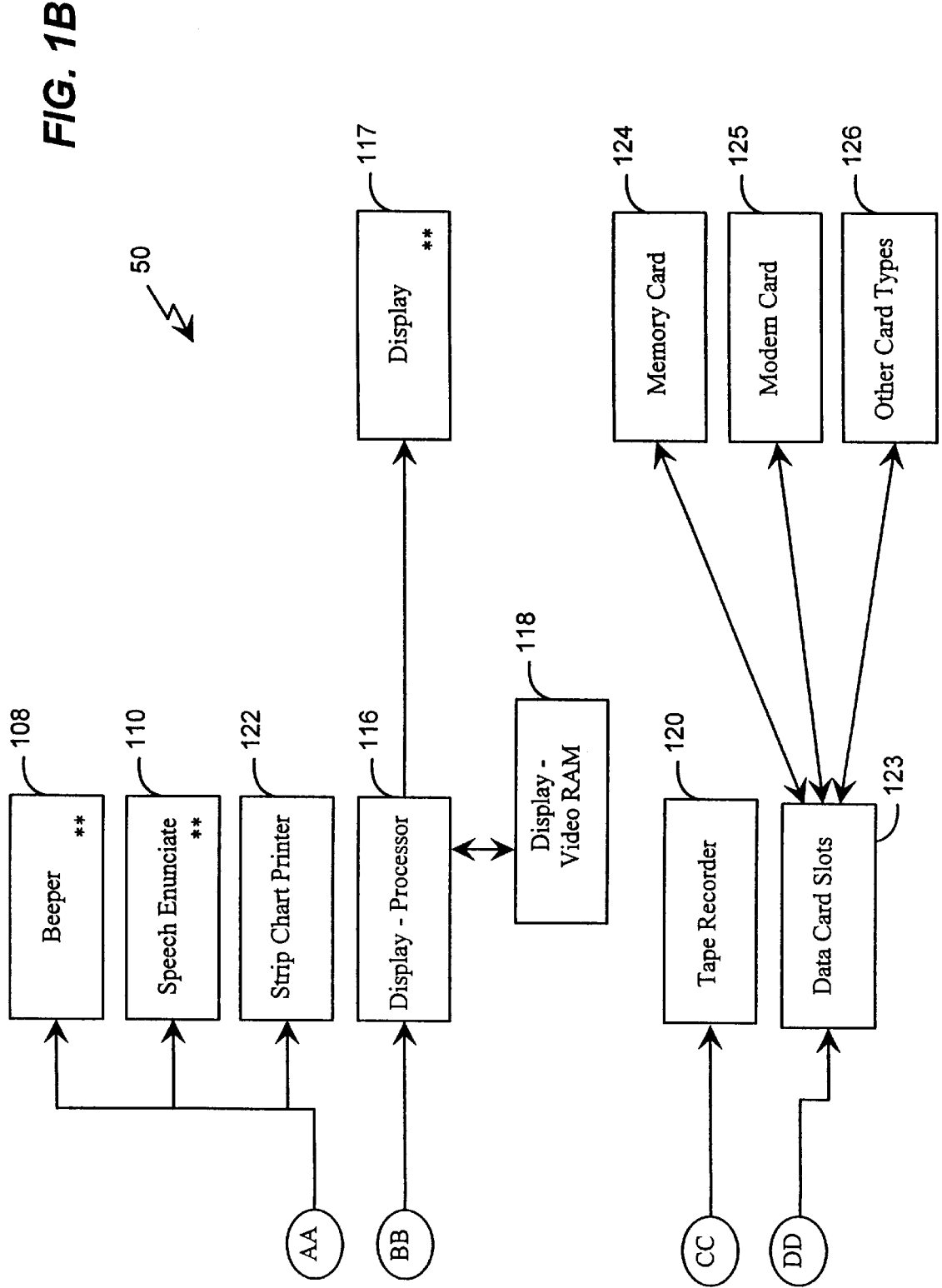

FIGS. 1A and 1B show a portable electronic unit 50, such as a defibrillator, incorporating an autotest system for automatically testing the unit during quiescent periods. While the autotest system of the present invention is shown and described herein for use with a defibrillator unit, those skilled in the art will recognize from this detailed description that the autotest system can be used to test various electronic devices where the testing of these devices is impractical during non-quiescent periods. Unless otherwise described in more detail herein, the circuits and components of the defibrillator unit are generally well-known to those skilled in the art, and any such circuits or components for providing the corresponding features described herein may be selected for use within the unit.

As shown in FIG. 1A, a patient is coupled to a defibrillator capacitor 103 through a transfer relay circuit 100 that selectively provides a charge stored in the capacitor to the patient, as described more fully below. A two lead impedance circuit 101 and a two lead ECG preamplifier circuit 102, coupled to the transfer relay 100, monitor vital signs of the patient. A transfer relay test circuit 104 coupled to the transfer relay 100 provides the circuit for testing the transfer relay. The transfer relay 100 and the transfer relay test circuit 104 are shown in more detail in FIG. 2 and are described more fully below.

The two lead impedance circuit 101 and the two lead ECG preamplifier circuit 102 are both coupled to a front end analog-to-digital ("A/D") converter 133, and together form a front end circuit 132. The front end circuit 132 isolates the patient from the unit 50 by converting signals input from the two lead impedance circuit 101 and the two lead impedance amplifier 102 into digital signals by the A/D converter 133.

A charging circuit 106 and a high voltage monitor 107, coupled to the defibrillator capacitor 103, provide and monitor the voltage, respectively, on the capacitor. A main central processing unit ("CPU") 111 for performing most tasks in the unit 50 is coupled to most components in the unit including the battery charging circuit 106, the front end A/D converter 133, a CPU memory 105, and a safety processor 112. The front end A/D converter 133 is preferably coupled to the main PCU 111 by means of optoelectronic devices such as LED/phototransistor pairs. The front end circuit 132 is shown in more detail in FIG. 3 and is discussed more fully below. The CPU memory 105 preferably includes RAM or static RAM ("SRAM"), programmable read-only memory ("PROM"), flash PROM, and electronically erasable programmable read-only memory ("EEPROM"). The safety processor 112 for ensuring safe defibrillator of the patient is directly coupled to the charging circuit 106 by means of an energy select circuit 109.

Since the unit 50 is portable, at least two rechargeable batteries A and B are provided to power the unit. The unit 50 preferably includes a battery voltage/charging circuit 131 for charging, switching, and monitoring the batteries A and B. The voltage/charging circuit 131 and its various charging, switching, and monitoring functions described in detail in U.S. Pat. No. 5,640,078, entitled "METHOD AND APPARATUS FOR AUTOMATICALLY SWITCHING AND CHARGING MULTIPLE BATTERIES," incorporated herein by reference. A power control circuit 129 having a power-on switch 129' is coupled to the batteries A and B. A real-time clock 113 for initiating the autotest system is coupled to both the power control circuit 129 and the main CPU 111. Operation of the power control circuit 129 and the real-time clock 113 are discussed more fully below.

An analog-to-digital ("A/D") converter 115 receives analog signals from various components within the unit 50, digitizes these analog signals and inputs them to the main CPU 111. For example, the battery voltage/charging circuit 131 coupled to the batteries A and B, monitors the voltage on the batteries and outputs a voltage signal to the A/D converter 115. Similarly, a temperature sensor 130 monitors the ambient temperature and provides a temperature signal to the A/D converter 115. A program voltage generator 128 coupled to the CPU memory 105, the main CPU 111, and the A/D converter 115, provides a regulated voltage to reprogram the flash PROM in the CPU memory.

The defibrillator unit 50 preferably includes several ports 114 for allowing at least three modules to couple to the main CPU 111. The modules are specifically designed for use with the unit 50 and allow the unit to provide additional features such as blood pressure monitoring. Several data card slots 123 for coupling PCMCIA cards to the main CPU 111, such as a memory card 124, a modem card 125, or other types of cards 126, can expand the memory, communications or other functionality of the unit 50.

As shown in FIG. 1B, the unit 50 also includes several operator feedback circuits, including a beeper 108 to provide warning beeps, a speech enunciator 110 for providing voice instructions to the operator, and a strip chart printer 122 (discussed more fully below), all coupled to the main CPU 111. A visual display 117, such as a flat liquid crystal display panel is coupled to a display processor 116. The display processor 116 is coupled to the main CPU 111 and to video display RAM or SRAM 118. Several switches 127, associated with the display 117 and other components in the unit 50, are coupled to the main CPU 111. A tape recorder 120 and an optional speech recorder 119 with speech record memory 121 (preferably SRAM), both for recording voices and ambient sounds during treatment of the patient, are coupled to the main CPU 111.

Referring now to FIGS. 4 through 8, an autorest routine 200 is shown that tests the functioning of the circuits and components of the unit 50. The autotest routine 200 is preferably stored in the PROM and/or flash PROM of the CPU memory 105 and executed primarily by the main CPU 111. Where a meaningful test exists, the autotest routine 200 tests each circuit in the unit 50 to ensure proper functional readiness of the unit 50 and allows the unit to perform its essential functions such as monitoring vital signals of the patient and properly delivering a shock to him or her. The basic or essential functions performed by the unit 50 during the normal mode of operation are referred to herein as the "essential functions" of the unit.

The autotest routine 200 is initiated when the time on the real-time clock 113 equals a previously selected autotest start time stored in the EEPROM of the CPU memory 105. The autotest start time is preferably set to a time when the unit 50 is not likely to be used for its essential functions, such as 4:00 a.m. An operator can stop the autotest routine 200 from executing by selecting an invalid autotest start time such as a negative time value.

The real-time clock 113 is preferably model no. RTC-72423 manufactured by Epsom America of Torrance, Calif., because this clock is pre-calibrated and relatively inexpensive. This particular clock can be set to provide an alarm output signal only at a selected time every hour. Consequently, at the selected time every hour, the real-time clock 113 provides the alarm output signal to the power-up control circuit 129 (i.e., the "RTC_VAKEUP" signal shown in FIG. 1A), which in turn provides a "COLD START" signal to the main CPU 111, powering up the CPU.

Figure 4A:
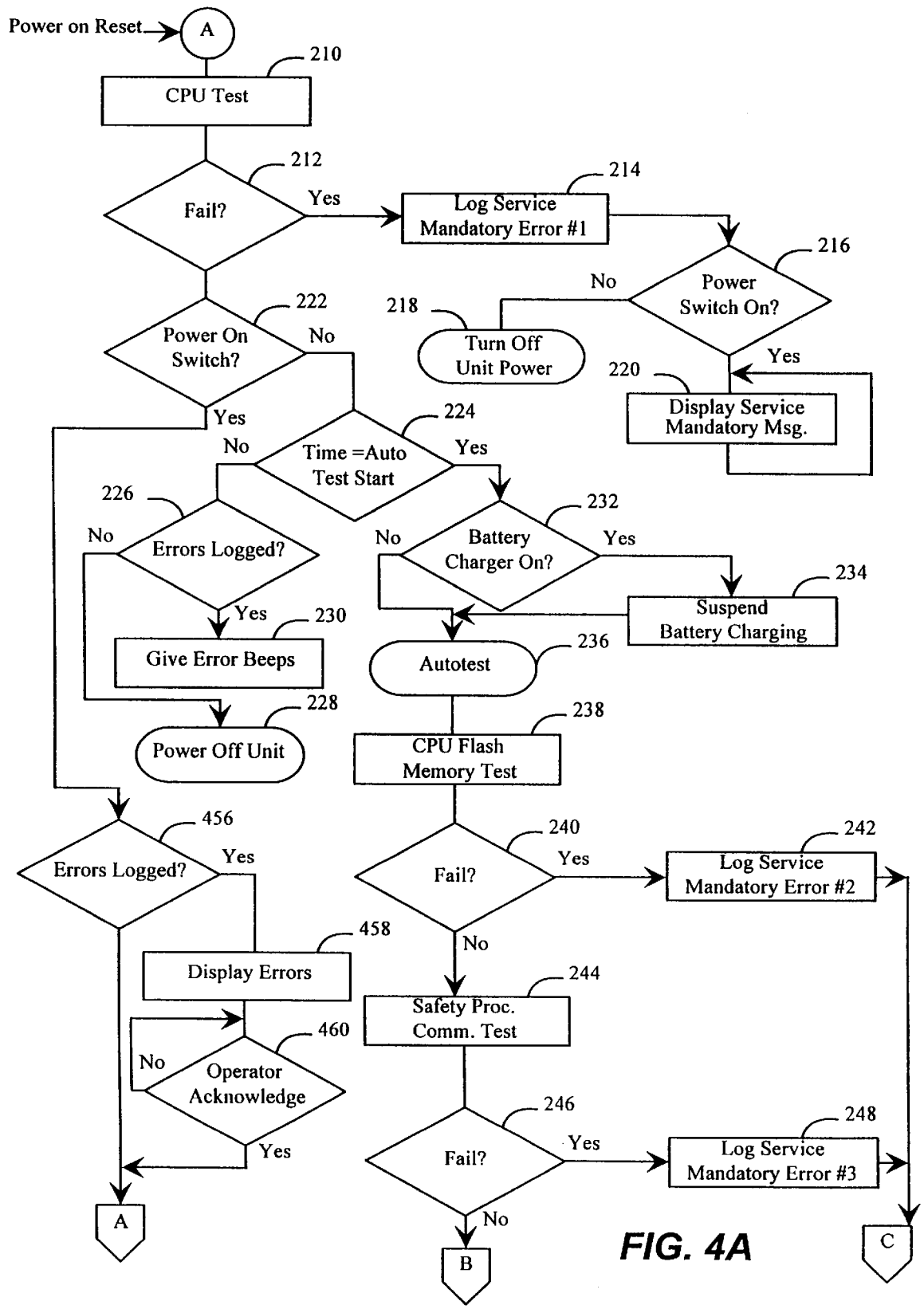
FIGS. 4A, 4B, 5A, 5B, 6A, 6B, 7A, 7B, and 8 are flowcharts of a method under the present invention of automatically testing the electrical components of the unit of FIGS. 1A and 1B.
Figure 4B:
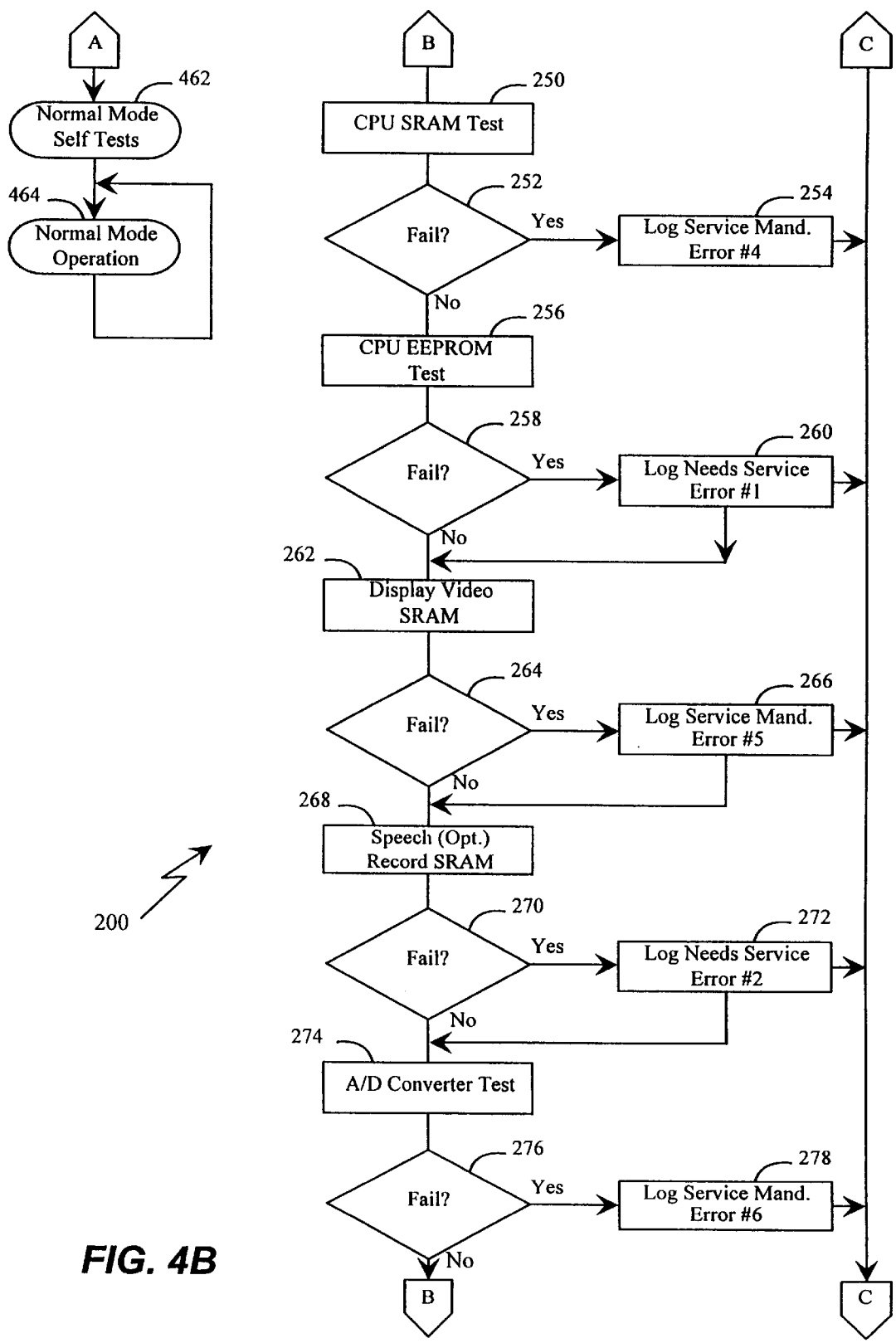

Referring to FIG. 4, after power-up of the main CPU 111, the CPU performs its standard power-up self-tests internal to the particular type of CPU in step 210. If the main CPU 111's self-tests fail (step 212), then the CPU "logs" the results of the particular test it failed by storing the results of the test with an appropriate code in the EEPROM of the CPU memory 105 in step 214. As used herein, "logging" refers to permanently storing in the EEPROM of the CPU memory 105 the results of a failed test to ensure that the results are not lost upon power-down of the unit 50.

The unit 50 preferably logs two general types of errors: "service mandatory" or "needs service" errors. A service error generally requires immediate attention by the operator for the unit to properly perform its essential functions. An example of a service mandatory error is when the batteries A and B installed in the unit 50 are so depleted of charge that they do not have sufficient energy to deliver a shock to a patient. A needs service error allows the unit 50 to perform its essential functions, but without some enhanced features, e.g., data recording or external communications. To identify the failed test and thus help identify which component of the unit 50 is malfunctioning, the main CPU 111 provides an error code such as a numeral to each logged error. Since the main CPU 111 performs most major operations of the unit 50, a defective CPU is a service mandatory error. Therefore, in step 214, the main CPU 111 logs a failure of the CPU self-test as a service mandatory error #1 if the CPU 111 executes well enough to perform this action.

After logging the service mandatory error #1 in step 214, the main CPU 111 determines in step 216 if the power switch 129' is on. If the power switch is not on (i.e., off), then in step 218 the main CPU 111 provides a signal to the power control circuit 129 that instructs the power control circuit to turn the power off to the unit 50, thus discontinuing the autotest routine 200. If the main CPU 111, in step 216, determines that the power switch 129' is on, then the main CPU 111 displays a service mandatory message on the display 117 in step 220. The displayed service mandatory message can include a message indicating that the CPU self-test failed.

If the CPU self-test 210 did not fail in step 212, then the main CPU 111 determines if the power switch 129' is on in step 222. If the power switch 129' is off, then the main CPU 111 determines in step 224 if the time on the real-time clock 113 equals the autotest start time. If the time on the real-time clock 113 does not equal the selected autotest start time in step 224, then the main CPU 111 determines in step 226 whether any errors have been logged. If no errors have been logged, then the main CPU 111 instructs the power control circuit 129 to power-down the unit 50 in step 228.

If the main CPU 111 determines that terrors have been logged in step 226, then in step 230, the main CPU 111 provides on appropriate signal to the beeper 108 causing the beeper to emit a short series of audible beeps indicating that the unit 50 has previously completed the autotest routine 200 and currently has malfunctioning components that have not been remedied. After emitting a series of beeps in step 230, the main CPU 111 instructs the power control circuit 129 to power down the unit in step 228.

Since the real-time clock 113 turns on the main CPU 111 once every hour, the main CPU 111 compares the current time on the real-time clock 113 to the autotest start time stored of the CPU memory 105 each hour. The autotest routine 200 is only initiated when the main CPU 111 determines that the autotest start time equals the current value on the real-time clock 113. If the autotest routine 200 has previously completed its series of tests and logged at least one error, the unit 50 provides the short series of beeps in step 230 every hour thereafter until the operator powers up the unit.

If the time on the real-time clock 113 equals the selected autotest start time in step 224, then the main CPU 111 determines in step 232 if the battery voltage/charging circuit 131 is "on," i.e., currently charging the batteries A and/or B. If the battery voltage/charging circuit 131 is on, then the main CPU 111 suspends the battery charging functions in step 234.

After suspending the battery charging functions in step 134, or if the battery voltage/charging circuit 131 is not on in step 232, then the main CPU 111 begins a series of primary autotest functions 236, beginning with testing the PROM and flash PROM of the CPU memory 105 in step 238. The PROM and flash PROM of the CPU memory 105 are preferably tested using a standard CRC test. The CRC test is preferably optimized for speed by using known techniques, such as by using an $x^{12}+x^5+x$ polynomial. If the main CPU 111 in step 240 determines that step 238 failed, then the CPU logs this failure as a service mandatory error #2 in step 242.

After the main CPU 111 first determines that a component failed its test and caused a service mandatory error, the CPU generally discontinues the autotest routine 200 since the malfunctioning component could skew any additional testing of components and thus produce inaccurate test results. Additionally, a full test of all the components of the unit 50 are preferably performed when the unit is serviced to correct the service mandatory error. Consequently, after the main CPU 111 logs the service mandatory error #2 in step 242, the autotest routine 200 discontinues any further testing of additional components within the unit 50 and the autotest routine continues as described below with respect to FIG. 8.

If the PROM and flash PROM of the CPU memory 105 successfully pass the CRC test, then the main CPU 111 in step 244 tests communications between itself and the safety processor 112. In step 244, the safety processor 112 initializes itself, performs its standard self-tests particular to the type of processor (similar to the self-tests performed by the main CPU 111), and outputs a signal reflecting the results of the self-tests to the main CPU 111. The main CPU 111 ensures that the signal from the safety processor 122 indicates that the safety processor successfully completed all of its self-tests. Thereafter, the safety processor and the main CPU 111 continually exchange messages to each other during the autotest routine 200, preferably 100 milliseconds apart, to indicate that each is itself functioning properly. If these messages are not sent and received as expected, i.e. at the appropriate intervals and in the appropriate form, or if the safety processor 112 failed its self-tests, then the safety processor or communications between the main CPU 111 and the safety processor are malfunctioning. In either case, the main CPU 111 determines that the test 244 failed in step 246, and the CPU consequently logs a service mandatory error #3 in step 248.

If the safety processor 112 passes its self-tests and communication signals between the main CPU 111 and the safety processor are appropriate, then the CPU tests the SRAM of the CPU memory 105 in step 250. The SRAM of the CPU memory 105 is tested using the standard walking pattern test. If the main CPU 111 determines in step 242 that the walking pattern test in step 250 failed, then the CPU logs this failure as a service mandatory error #4 in step 254.

If the SRAM successfully completes the walking pattern test, then the main CPU 111 tests the EEPROM of the CPU memory 105 in step 256. The EEPROM memory is tested using a standard checksum test. The EEPROM memory generally stores non-critical data, and thus a simple and efficient checksum error test can be performed thereon. If the EEPROM, however, is used to store critical data, then a more rigorous CRC test is preferably performed thereon. If the main CPU 111 determines in step 258 that the test 256 failed, then the CPU logs thus failure as a needs service error #1 in step 260.

Since the EEPROM memory, or other tested components noted below, are not required to perform the essential functions of the unit 50, the autotest routine 200 continues to test the remaining components in the unit 50 following the logging of a needs service error. Consequently, after the main CPU 111 logs the needs service error #1 in step 260, or if the EEPROM successfully completed the checksum test, the CPU tests the display video RAM 118 in step 262. The display video RAM 118 is tested using the walking pattern test. If the main CPU 111 determines in step 264 that the video display RAM 118 failed its test, then the CPU logs this failure as a service mandatory error #5 in step 266.

The autotest routine 200 continues despite finding a service mandatory error after testing the video display RAM 118 because continued testing of the unit 50 will provide meaningful results, i.e., malfunctioning video display RAM will not produce inaccurate test results. Thus, after the main CPU 111 logs the needs service error #5 in step 266, or if the display video RAM 118 successfully completes the walking pattern test, then the CPU performs the walking pattern test on the speech recording SRAM 121 in step 268. If the main CPU 111 determines in step 270 that the walking pattern test 268 of the speech record SRAM 121 failed, then the CPU logs this failure as the needs service error #2 in step 272.

After the main CPU 111 logs the needs service error #2 in step 272 or if the speech record SRAM 121 successfully completes the walking pattern test, then the CPU tests the A/D converter 115 in step 274. The main CPU 111 tests the A/D converter 115 by directing the charging circuit 106 to provide a reference voltage signal to the A/D converter 115 and then comparing the output from the A/D converter. If the main CPU 111 receives an input signal from the A/D converter 115 which differs from the expected value of the reference voltage signal from the charging circuit 106, then either the A/D converter or the charging circuit are malfunctioning. In either event, the main CPU 111 determines that the A/D converter test 274 fails in step 276 and consequently logs a service mandatory error #in step 278.

Figure 5A:
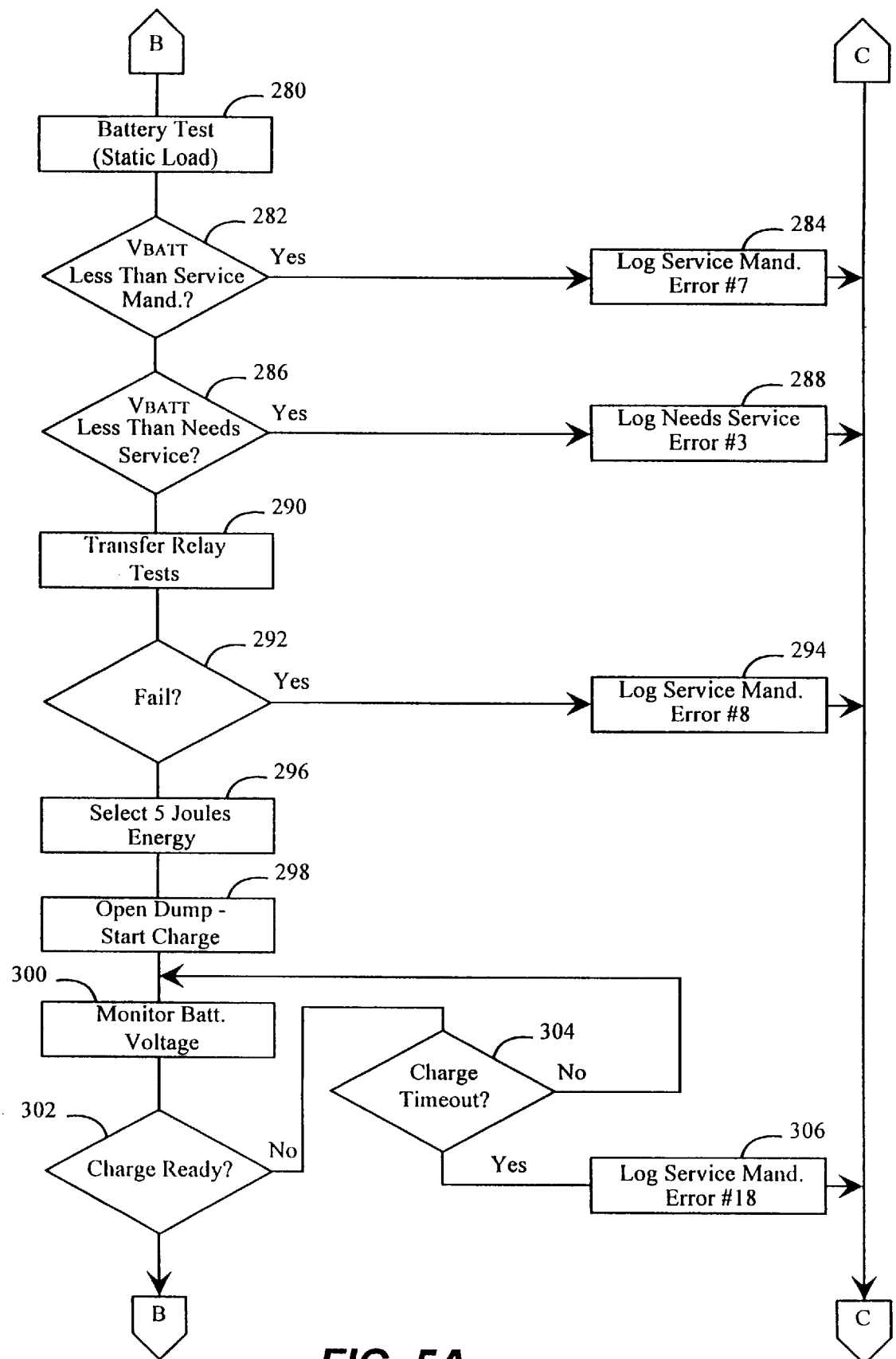
Figure 5B:
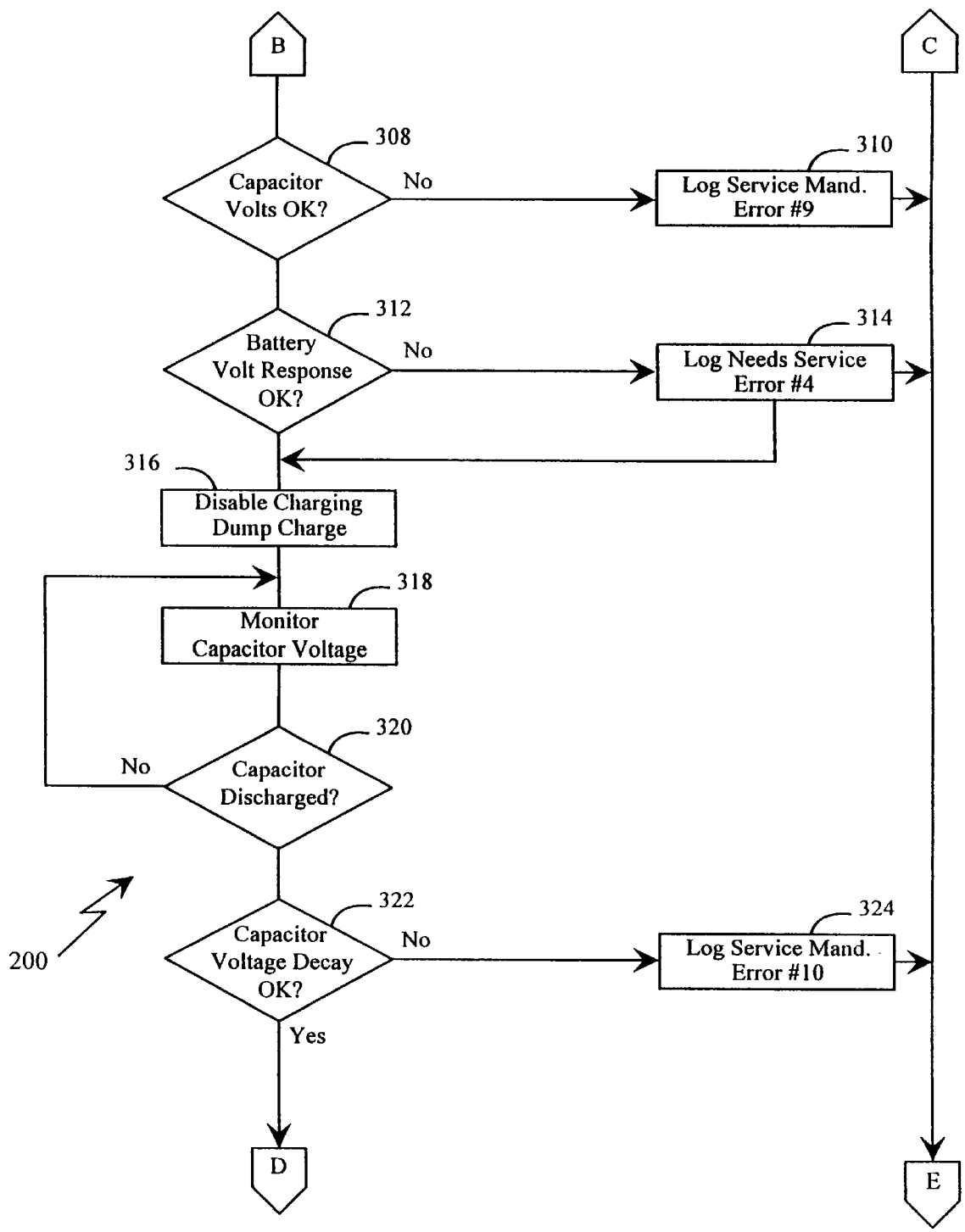

Referring now to FIG. 5, if the main CPU 111 determines that the A/D converter test 274 was successfully completed, then the CPU tests the batteries A and B in step 280. The battery voltage/charging circuit 131 monitors the terminal voltages on the batteries A and B and outputs appropriate analog voltage signals to the A/D converter 115, which converts these analog signals into digital signals that the main CPU 111 analyzes. The main CPU 111 compares the terminal voltages on the batteries A and B to at least three threshold voltages; a "needs service" threshold, a "service mandatory" threshold, and a "battery removed" threshold. The needs service and service mandatory thresholds are estimates of the percent capacity at various load currents in the unit 50 for a given battery.

The batteries A and B are preferably rechargeable batteries such as Model No. LSC2012DVBNC, manufactured by Panasonic®. This particular battery has a full capacity of 13.5 volts and a maximum safe depleted capacity (or "service mandatory" capacity) of approximately 8.5 volts. As a result, the service mandatory threshold, i.e., the lowest safe threshold, is set above 8 volts for a 10-amp load current. This lowest threshold is set well above 0 volts to prevent a battery from being nearly completely depleted because batteries nearly fully drained of their charge are difficult to recharge and can be damaged. Additionally, any battery having a terminal voltage above the service mandatory threshold can still deliver a reliable charge to a patient, which for a defibrillator can prove life-saving. With a 10-amp load current, the needs service threshold is approximately 9.75 volts. The battery removed threshold is set at a very low voltage, but not necessarily 0 volts, because of internal bias within the unit 50 creating a background a greater than 0 volts. A description of establishing and monitoring these and other battery voltage thresholds is described more thoroughly in the previously cited co-pending application.

In step 282, if the main CPU 111 determines that the terminal voltage measured on both the batteries A and B is below the service mandatory threshold, then the CPU recognizes that the batteries contain insufficient charge to allow the unit 50 to perform if essential functions and consequently logs a service mandatory error #7 in step 284. If the main CPU 111 determines that the measured voltage on both of the batteries A and B is less than the needs service threshold in step 286, then the CPU recognizes that the unit 50 has sufficient power to performs its essential functions (for a limited time) but logs a needs service error #3 in step 288.

After determining that the terminal voltages on both the batteries A and B are below the service mandatory threshold, the main CPU 111 compares the terminal voltages to the battery removed threshold. If either of the batteries are below the battery remove threshold, then the main CPU 111 can provide an appropriate service mandatory error instruction with the service mandatory error #7 indicating which battery has been removed. The service mandatory error #7 and the needs service error #3 also provide an indication as to which of the batteries A and B are service mandatory and/or needing service, thus allowing the operator to replace or charge the appropriate battery.

Figure 2:
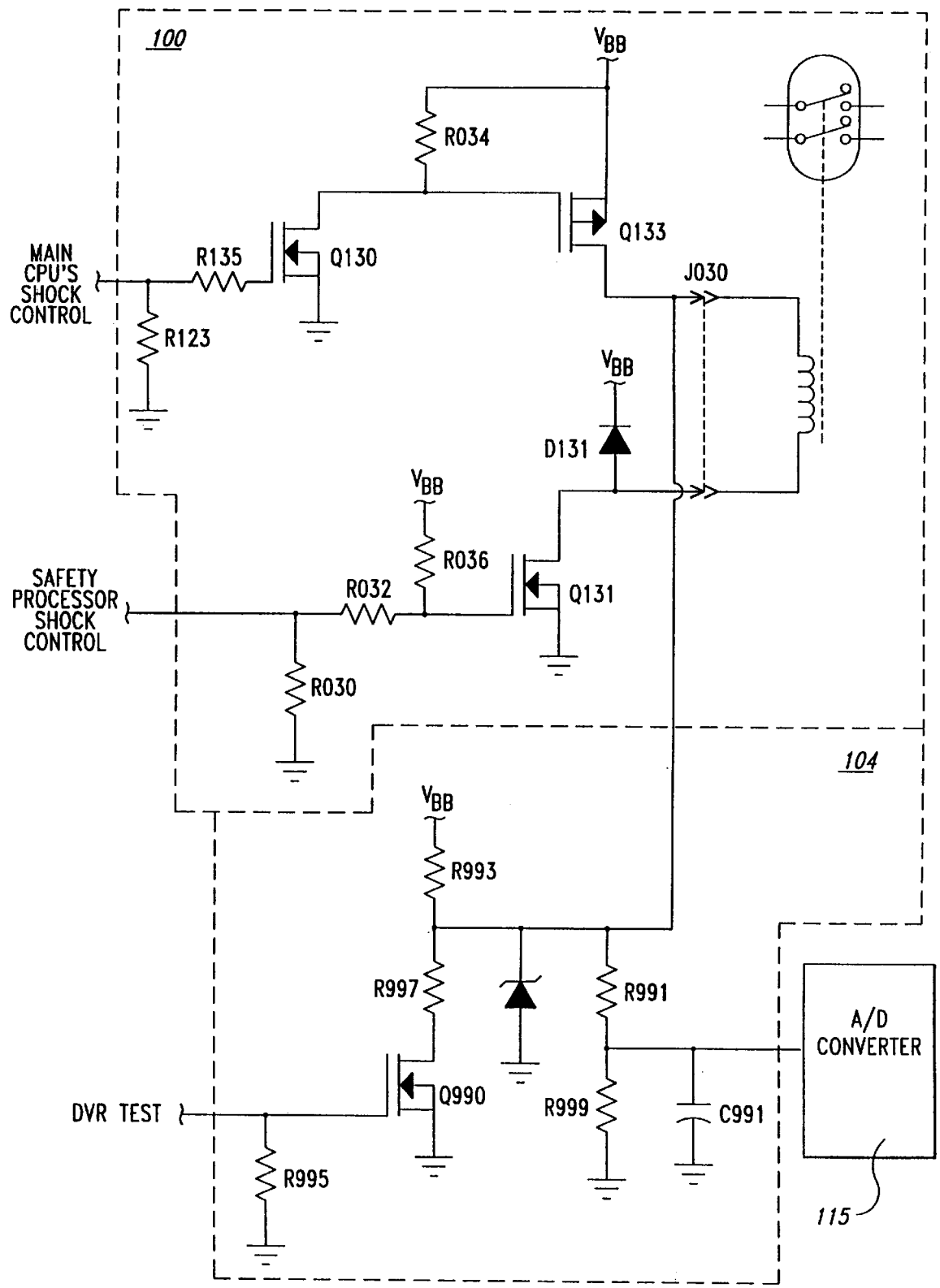
FIG. 2 is a schematic diagram of a transfer relay circuit and transfer relay test circuit for the unit of FIGS. 1A and 1B.

If either of the batteries A and B have a terminal voltage greater than the service mandatory threshold, then the main CPU 111 tests the transfer relay circuit 100 in step 290. Referring to FIG. 2, the main CPU 111 tests the transfer relay circuit 100 by using the transfer relay test circuit 104. To ensure that a patient receives only a shock having an appropriate amount of energy and at an appropriate time, both a shock control signal from the main CPU 111 and a shock control signal from the safety processor 112 must be received by the transfer relay circuit 100 to switch a charge stored on the defibrillator capacitor 103 to the patient. The transfer relay test circuit 104, under control of the main CPU 111, performs two tests of the transfer relay circuit 100. In the first test, the main CPU 111 disables its shock control signal (i.e., sets it to a low voltage value), shown input to a transistor Q130 through a resistor R135 in FIG. 2. The main CPU 111 also directs the safety processor 112 to disable its shock control signal, which is input to a transistor Q131 through a resistor R032. When the main CPU 111 and the safety processor 112 disable their shock control signals, the transistors Q130 and Q131, and a transistor Q133 coupled to the transistor Q131 are all switched off.

Thereafter, the main CPU 111 supplies a low voltage DVR test signal coupled to a transistor Q990 in the transfer relay test circuit 104, which switches off this transistor. After switching off the transistors Q130, Q131, Q133, and Q990, the A/D converter 115 measures the voltages at the drains of the transistors Q131 and Q133 at a node between a voltage divider network consisting of resistors R991 and R999. Because all of the transistors Q130, Q131, and Q990 are off, a voltage $V_{BB}$ applied to a resistor R993 is not shunted to ground through one or more of these transistors, but instead through the resistors R991 and R999. Consequently, the A/D converter 115 outputs a high voltage level to the main CPU 111 as measured at the node between the resistors R991 and R999. If the main CPU 111 recognizes a low voltage output from the A/D converter 115 during this first test, the transistor Q131 or its driving circuitry (including a diode D131 and a resistor R036) are likely malfunctioning.

In the second test of the transfer relay circuit 100, the main CPU 111 provides a high voltage DVR test signal to the transistor Q990 of the transfer relay test circuit 104, turning this transistor on. When the transistor Q990 is on, the voltages at the drains of the transistors Q131 and Q133 should be pulled down to a low voltage level determined by a voltage divider circuit consisting of the resistor R993 and a resistor R997. Consequently, the A/D converter 115 outputs a low voltage level to the main CPU 111 as measured at the node between the resistors R991 and R999. If the main CPU 111 recognizes a high voltage output from the A/D converter 115 during the second test, the transistor Q133 or its driving circuitry (including a resistor R034) are likely malfunctioning. If either of the above first or second tests of the transfer relay circuit 100 fail in step 292, then the main CPU 111 logs this failure as a service mandatory error #8 in step 294.

While not shown in FIG. 5, the autotest routine 200 can also test the transistors Q13, Q131 and Q133 in their closed condition. In this additional, optional test of the transfer relay circuit 100, the main CPU 111 first measures the voltage on the defibrillator capacitor 103 by means of the high voltage monitor 107 and insures that the capacitor has a 0 voltage. For reasons of safety, the main CPU 111 must insure that the transfer relay circuit 100 does not externally discharge any charge on the defibrillator capacitor 103 during testing. Then, the main CPU 111 and the safety processor 112 provide their shock control signals to the transistors Q130 and Q131, respectively, thereby actuating the transfer relay of the transfer relay circuit 100. Concurrently, the main CPU 111 measures the voltage output from the transfer relay circuit 100 to determine if the transfer relay actuated in response to the shock control signals. If not, the main CPU 111 logs an appropriate service mandatory error.

If the transfer relay circuit 100 successfully completes the above two tests, then the main CPU 111 tests the defibrillator capacitor charging functions of the unit 50. During the charging functions, the charges on the batteries A and B are provided to the defibrillator capacitor 103 by means of the charging circuit 106. In step 296, the safety processor 112 first removes an inhibit signal from the charging circuit 106, providing half the signals necessary to open an internal dump relay (not shown) for dumping charge from the batteries A and B to the defibrillator capacitor 103. Thereafter, the main CPU 111 provides a command signal to the internal dump relay to open this relay and allow the defibrillator capacitor 103 to begin charging. The main CPU 111 in step 286 also instructs the safety processor 112 to command the energy select circuit 109 to select a low value of energy, preferably 5 joules (although other values could be used), and provide an energy charge signal to the charging circuit 106. The charging circuit 106, in response to the selected 5 joules energy charge signal, begins charging the defibrillator capacitor 103 in step 298.

As the defibrillator capacitor 103 charges, the main CPU 111 monitors the voltage on the batteries A and B in step 300. In step 302, the main CPU 111 determines if the batteries A and B have applied the selected 5 joules of energy to the defibrillator capacitor 103. If not, then the main CPU 111 in step 304 determines if a selected time-out for charging the defibrillator capacitor 103 has expired. If the time-out has not expired, the autotest routine 200 loops back to step 300 so that the main CPU 111 continues monitoring the voltage on the batteries A and B and determining if the batteries have applied a charge to the defibrillator capacitor 103 equal to 5 joules in step 302. As a result of this loop in the autotest routine 200, the main CPU 111 determines how long it takes for the batteries A and the charging circuit 106 to apply to the selected amount of energy to the defibrillator capacitor 103. If the time-out expires in step 304 before the batteries A and B have applied 5 joules to the defibrillator capacitor 103, then the main CPU 111 recognizes that the unit 50 is unable to properly charge the defibrillator capacitor and consequently logs a service mandatory error #18 in step 306. A failure in charging the defibrillator capacitor 103, and thus the service mandatory error #18, can reflect a malfunction in the charging circuit 106, the energy select circuit 109, a failure to provide or coordinate the charge enable command signal from the main CPU 111 with the removal of the inhibit signal and application of the energy charge signal from the safety processor 112.

During charging of the defibrillator capacitor 103, the main CPU 111 monitors the voltage on the batteries A and B (by means of the battery voltage charging circuit 131 and the A/D converter 115) in step 300. If the main CPU 111 recognizes an excessive drop in the terminal voltage of either of the batteries A and B during the charging of the defibrillator capacitor 103 in step 312, then the CPU recognizes that the battery may be losing its effective capacity to hold a charge and consequently logs a needs service error #4 in step 314.

After the defibrillator capacitor 103 receives an appropriate charge in step 302, the main CPU 111 measures and monitors a voltage signal output from the high voltage monitoring circuit 107 that indicates the voltage on the capacitor. In step 308, if the voltage on the defibrillator capacitor 103 is not sufficient to provide a shock to a patient of 5 joules then the main CPU 111 logs a service mandatory error #9 in step 310. After the defibrillator capacitor 103 has been charged the main CPU 111 discontinues applying the charging enable signal to the charging circuit 106 and the dump relay open signal to the dump relay in step 316. In step 316, the main CPU 111 also commands the safety processor 112 to resume applying its charging inhibit signal to the charging circuit 106. As a result, the dump relay closes, internally discharging the 5 joules of energy in the defibrillator capacitor 103 to the unit 50. During this discharge, the main CPU 111 continues to monitor the voltage on the defibrillator capacitor 103 in step 318 as the terminal voltage on the capacitor decays back towards zero in step 320. The terminal voltage on the capacitor 103 should decrease at a selected time constant. If the voltage during discharge of the capacitor 103 is unacceptable in step 322, the main CPU 111 logs a service mandatory error #10 in step 324.

Figure 6A:
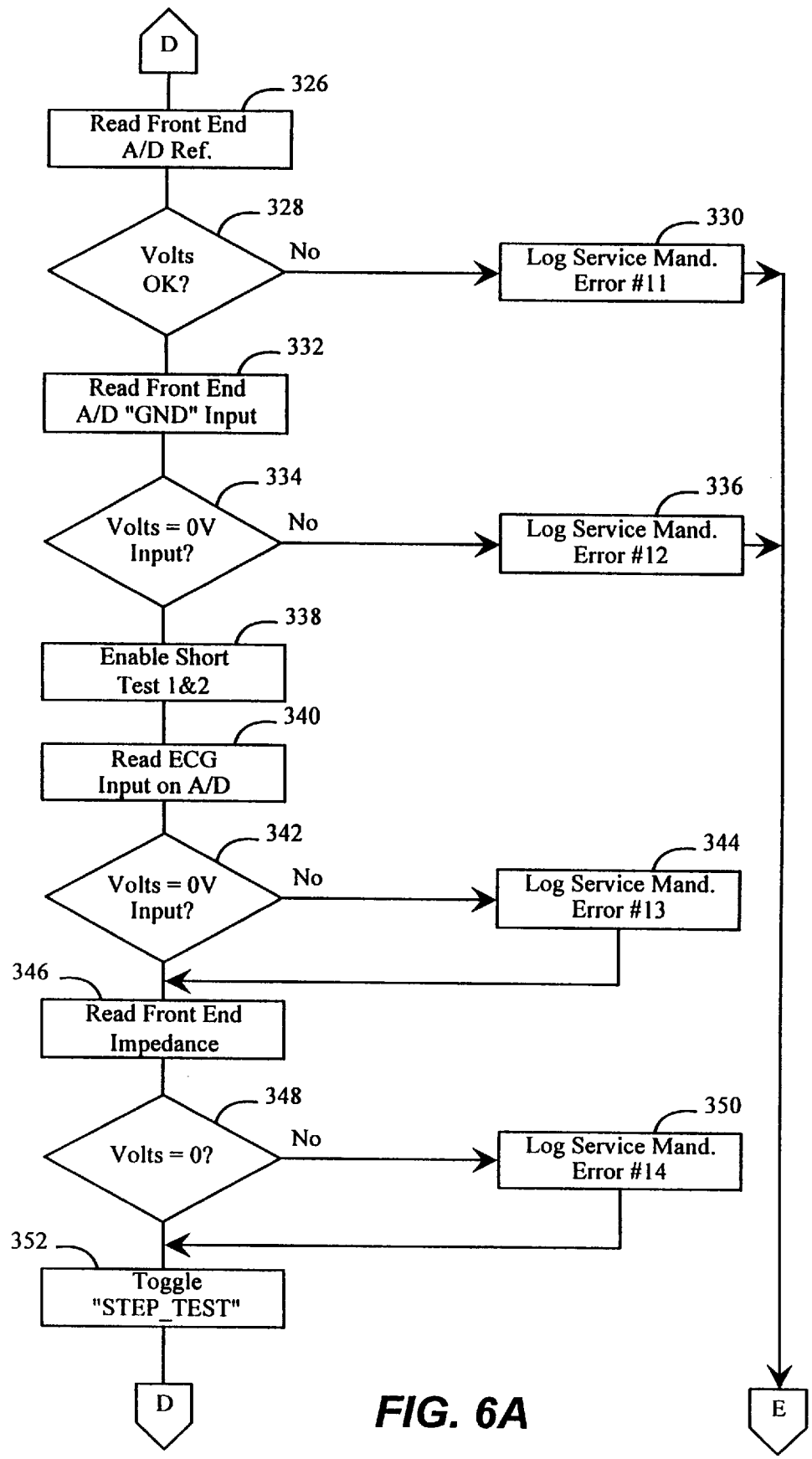
Figure 6B:
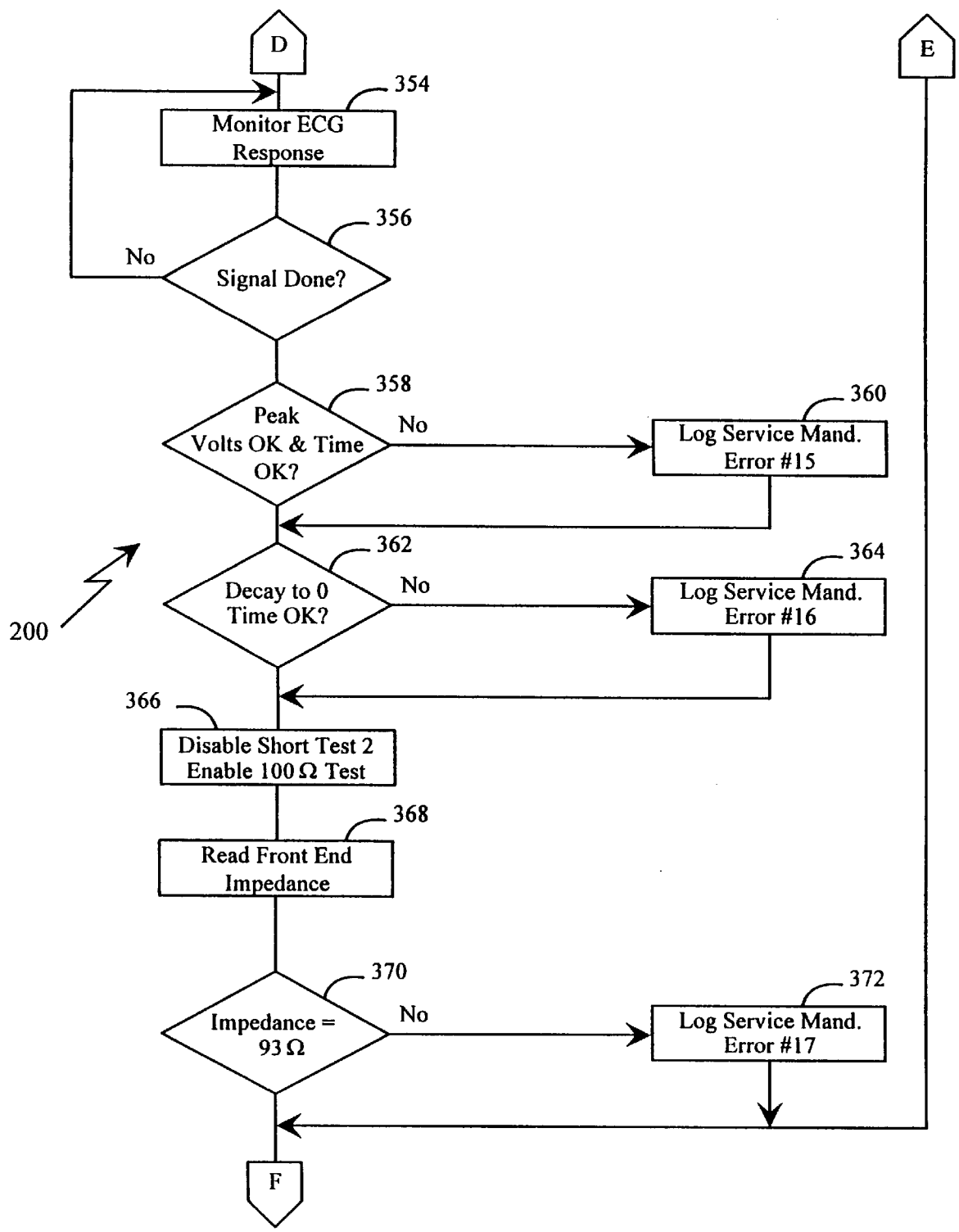

Referring now to FIG. 6, the main CPU 111 tests the two lead front end circuit 132 by testing the front end A/D converter 133, the two lead impedance circuit 101 and the ECG preamplifier circuit 102. The main CPU 111 begins testing the front end A/D converter 133 of the front end circuit 132 by applying a reference voltage of 2.5 volts to A/D converter. The main CPU 111 monitors the output of the A/D converter 133 in response to this 2.5 reference voltage in step 326 and determines in step 328 if the CPU measures a corresponding 2.5-volt signal. If not, then the main CPU 111 logs a service mandatory error #11 in step 330.

If an appropriate 2.5-volt signal is measured from the front end A/D converter 133 by the main CPU 111, then the CPU measures the grounded inputs to the A/D converter to determine if they are equal to ground (i.e., approximately equal to 0 volts) in step 334. If not, then the main CPU 111 logs a service mandatory error #12 in step 336.

If the main CPU 111 recognizes 0-volt signal from the grounded inputs to the front end A/D converter 133, then the CPU tests the two lead impedance circuit 101 and the two lead ECG preamplifier circuit 102. The main CPU 111 tests the two lead ECG impedance circuit 101 by first shorting the input to this circuit and then injecting a known signal at the input to the circuit, and measuring the responses therefrom. The main CPU 111 tests the two lead ECG preamplifier circuit 102 by also shorting the input to this circuit, but then applying a known pulse to the input of the circuit, and measuring the responses output therefrom.

Figure 3:
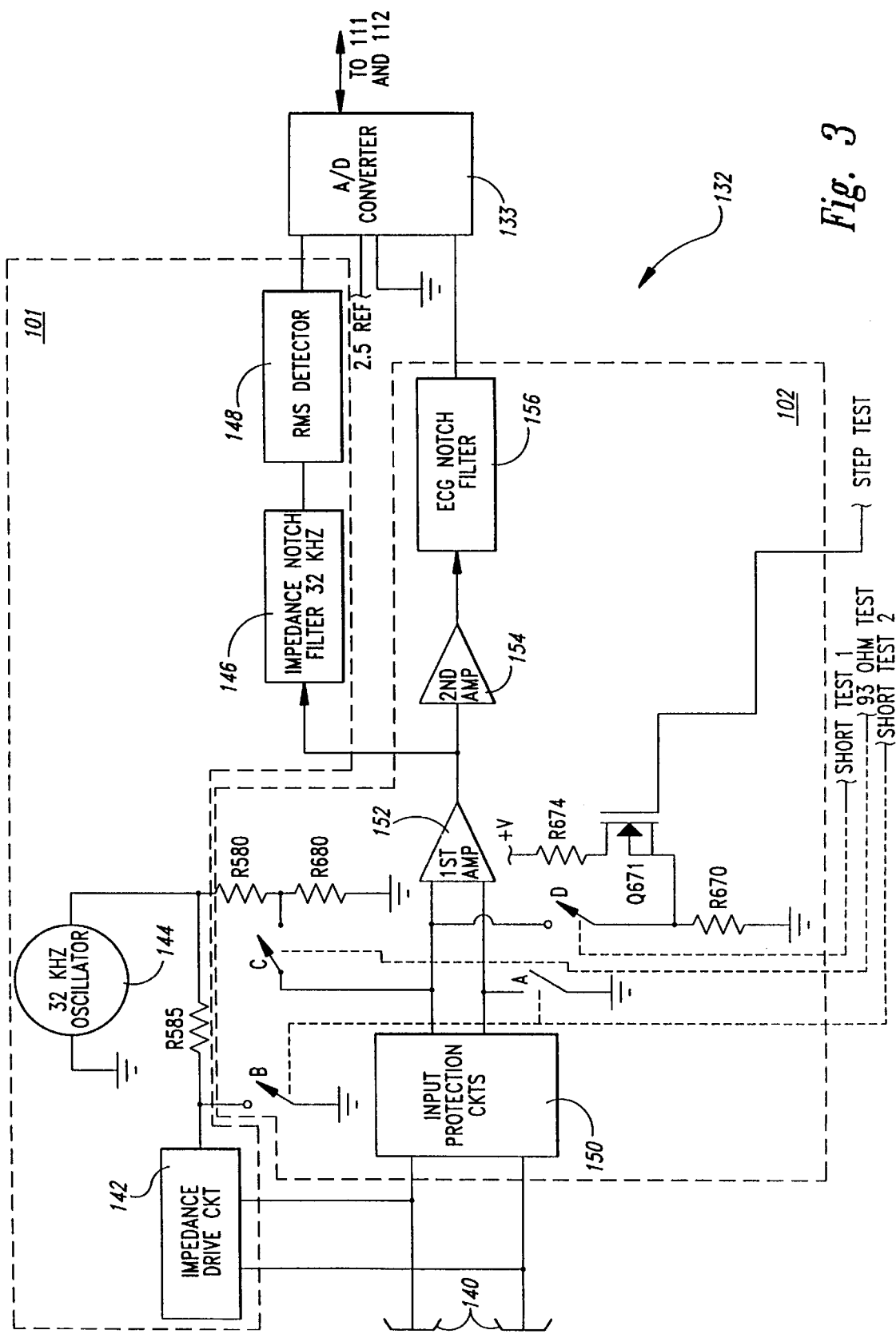
FIG. 3 is a partial schematic, partial block diagram of a front end circuit for the unit of FIGS. 1A and 1B.

Referring to FIG. 3, the main CPU 111 begins testing the two lead impedance circuit 101 and the two lead ECG preamplifier lead 102 by effectively providing a zero volt input signal to both of these circuits. The main CPU 111 instep 338 applies a short test 1 signal to a which D and a short test 2 signal to switches A and B. In response thereto, the switches A and D close, shorting lower and upper input leads to a first amplifier 152 of the ECG circuit 102 to ground. Similarly, the switch B closes, shorting a 32 kilohertz oscillator 144 and an impedance drive circuit 142 both coupled thereto to ground. Consequently, a pair of patient electrodes 140, coupled to the impedance drive circuit 142 and input protection circuits 150, are no longer driven by the impedance drive circuit, thus providing a zero volt input to the two lead impedance circuit 101 and the two lead ECG preamplifier circuit 102.

The output of the two lead ECG preamplifier circuit 102 is centered at a "mid-range" value for the range of outputs from the front end A/D converter 133. The front and A/D converter 133 is preferably of a type that provides 1024 increments wherein the highest amplitude analog input to the A/D converter produces a decimal output equal to 1024. Thus, a mid-range value from this front end A/D converter 133 would be approximately a decimal output of 512. Consequently, for a zero volt input to the two lead ECG preamplifier circuit 102, the main CPU 111 reads the corresponding output from the ECG preamplifier circuit (as digitized by the A/D converter 133) in step 340, and determines in step 342 whether an output from the preamplifier circuit is approximately equal to a decimal value of 512. If not, then the main CPU 111 logs a service mandatory error #13 i step 344.

Since the two lead A/D converter 133 satisfactorily passed the above tests (steps 326, 328, 332, and 344), the A/D converter is likely operating properly. Therefore, although both the two lead impedance circuit 101 or the two lead ECG preamplifier circuit 102 are critical for the essential functions of the unit 50 and a malfunction of either circuit results in a service mandatory error, both circuits may be rigorously tested under the autotest routine 200 without aborting the routine after the first service mandatory error is recognized. This is because of the signals output from the tests through the A/D converter 133 are presumably accurate tests results, and since the front end circuit 132 is an isolated circuit within the unit 50, a malfunction within the front end circuit will not affect the testing of other components within the unit. Consequently, a series of tests may be performed on the two lead impedance circuit 101 and the two lead ECG preamplifier circuit 102, each of which may result in a separate service mandatory error and which will help a technician locate and correct an error in the front end circuitry 132.

Consequently, even if the main CPU 111 determines that the signal output from the ECG preamplifier circuit 102 does not equal a mid-range value and is thus a service mandatory condition, the autotest routine 200 continues by reading a signal output from the front end impedance circuit 101 in step 346. The two lead impedance circuit 101 preferably provides a 0-ohm output for a 0-volt input. Therefore, the main CPU 111 determines in step 348 whether the output of the two lead impedance circuit 101 equals 0 ohms in response to the zero volt input caused the shorting of the inputs to the impedance circuit. If the signal output from the two lead impedance circuit 101 does not equal 0 volts in step 348, the main CPU 111 logs a service mandatory error #14 in step 350.

After reading the signals output from the two lead impedance circuit 101 and the two lead ECG preamplifier circuit 102 in response to a 0 volt input, the main CPU 111 begins a step test to check the frequency and gain of first and second amplifiers 152 and 154, respectively, of the preamplifier circuit. The main CPU 111 begins this step test in step 352 by applying the short test 2 signal to the switch B, closing it and thereby effectively disconnect the two lead impedance circuit 101 from the two lead ECG preamplifier circuit 102 by shorting the impedance circuit to ground. The main CPU 111 then applies a step test signal to a transistor Q671 of the two lead ECG preamplifier circuit 102, turning this transistor on. Concurrently, the main CPU 111 applies the short test signal to the switch D, closing it and causing a high voltage ($^+$V) to be applied through a resistor R674 and the transistor Q671 to the upper lead of the first amplifier 152.

Shortly thereafter, the main CPU 111 discontinues applying the step test signal to the transistor Q671, turning this transistor off. Since the switch D is still closed, the upper lead of the first amplifier 152 is pulled to ground through a resistor R670. This closing and opening of the transistor Q671 causes an analog voltage pulse which goes high toward a value of $^+$V when the main CPU applies the step test signal to close the transistor, and then low as the CPU discontinues applying the step test signal, thereby opening the transistor. This analog pulse is applied by the first and second amplifiers 152 and 154, respectively, and is input to an ECG notch filter 156. The ECG notch filter 156 essentially differentiates the analog pulse and provides a differ- entiated signal to the main CPU 111 through the front end A/C converter 133.

During the step test, the front end A/D converter 133 samples the output from the ECG notch filter 156 at a rapid rate to capture the peak value of the analog voltage pulse, and several samples surrounding the peak to indicate the time the two lead ECG preamplifier circuit 102 takes to reach the peak high value and decay back to a low or zero value. During the step test, the main CPU 111 monitors the output of the ECG notch filter 156 in step 354 stores the samples from the A/D converter 133 in the CPU memory 105, and determines in step 356 when the step test is complete. If the test is not complete, the main CPU 111 loops back and continues to monitor the output of the two lead ECG preamplifier circuit 102 in step 354.

After the step test has been completed, the main CPU 111 retrieves the samples from the CPU memory 105 and measures the peak voltage from the two lead ECG preamplifier circuit 102 and the time the preamplifier circuit took to reach the peak value in step 358. The time the two lead ECG preamplifier circuit 102 took to get to its peak value is an indication of the high end frequency limits of the ECG notches filter 156. The amplitude at the peak is an indication of the gain of the two lead ECG preamplifier circuit 102. If either the peak of time to reach the peak are unacceptable, then the main CPU 111 logs a service mandatory error #15 in step 360. Thereafter, or if the response from the preamplifier circuit 102 is acceptable, the main CPU 111 measures the time the two lead ECG preamplifier circuit 102 took to decay back to the lower or zero value. This decay time is an indication of the low end frequency response of the ECG notch filter 156. If the main CPU 111 measures an unacceptable decay time, then the CPU logs a service mandatory error #16 in step 364.

Thereafter, the main CPU 111 disables applying the short test 2 step 366, causing the switch C to close. The 32-kilohertz oscillator 144 applies a signal through a pair of resistors R580 and R680 coupled in series between the oscillator and ground. The 93-ohm impedance signal is established by the resistors R580 and R680, and this signal is applied from a node therebetween through the switch C, to the upper input lead of the first amplifier 152. The 93-ohm impedance signal is amplified by the first amplifier 152, and passed through an impedance notch filter 146, a root mean squared ("RMS") detector 148, and the front end A/D converter 133 before being input to the main CPU 111. The main CPU 111 reads the impedance value from the front end A/D converter 133 in step 368 and determines if it is equal to about 93 ohms in step 370. If the main CPU 111 determines in step 370 that the measured impedance output from the two lead impedance circuit 101 is not equal to about 93 ohms, then the CPU logs this failure as a service, mandatory error #17 in step 372.

Figure 7A:
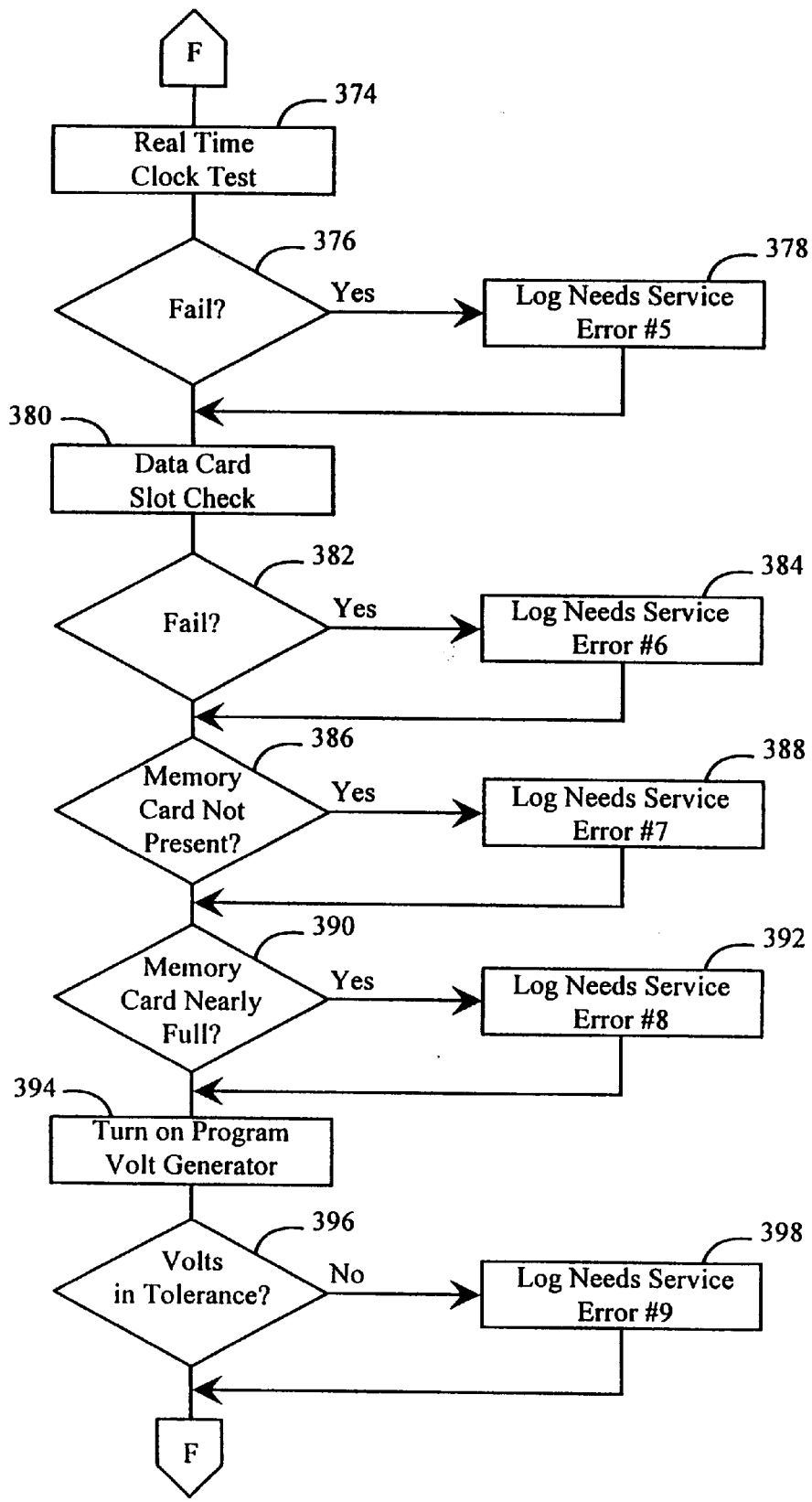
Figure 7B:
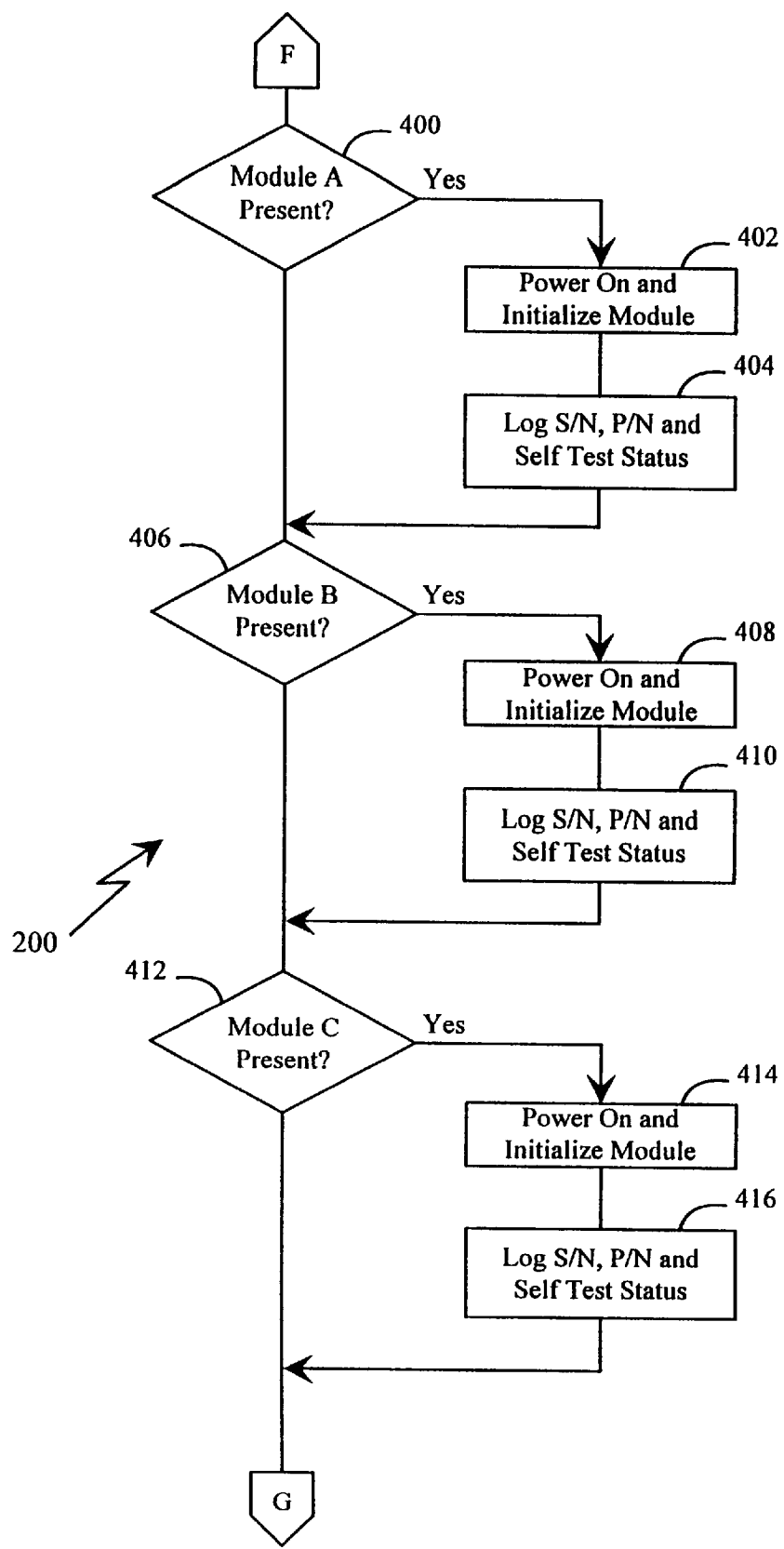

Referring now to FIG. 7, the CPU tests the real-time clock 113 in step 374. The main CPU 111 tests the real-time clock 113, after the main CPU 111 logs any of the service mandatory errors #11, #12 or #17, or if the impedance circuit 101 passed the 93-ohm test, by comparing its output to a CPU clock (not shown) to determine if the real-time clock and the CPU clock are counting off seconds at approximately equivalents. If the main CPU 111 determines in step 376 that the test of the real-time clock 113 fails in step 374, then the CPU logs this failure as a needs service error #5 in step 378.

In step 380, the main CPU 111 checks the functioning of the data card slots 132. If the main CPU 111 determines in step 382 that one or more of the data card slots 132 are malfunctioning (e.g., leads therein are shorted), the CPU logs this failure as a needs service error #6 in step 384. In step 386, the main CPU 111 determines if the memory card 124 is present. If the memory card 124 is not present, then the CPU logs this absence of the memory card as a needs service error #7 in step 388. If the memory card 124 is present, the main CPU 111 in step 390 determines if the memory card is nearly full. If the main CPU 111 determines that the memory card 124 is nearly full, then the CPU logs this error as a needs service error #8 in step 392. The autotest routine 200 may include additional steps (not shown) or testing other types of data cards, such as testing for malfunction in the modem card 125, or whether the batteries in a battery-backed SRAM card have sufficient voltage.

In step 394, the main CPU 111 turns on the program voltage generator 128. In step 396, the main CPU 111 monitors the voltage output from the program voltage generator 128 (as digitized by the A/D converter 115) to determine if the voltage signal output from the program voltage generator equals its preset voltage (e.g., 12 volts). If not, then the main CPU 111 logs this failure as a needs service error #9 in step 398.

In step 400, the main CPU 111 tests the module ports 114 by first determining if a module is present in the first module port (port a). If a module is present in the module port A, then the main CPU 111 powers on and initializes the module therein in step 402. The main CPU 111 interrogates the module present in the port A and logs its serial number, part number, software version number (if any), and the status of any self-tests of the module in step 404. If the module in the port A does not respond or if it responds with a status indicating an error, the main CPU 111 logs these errors in step 404.

The main CPU 111 similarly determines if a module is present in the second module port 114 (port B) in step 406, powers on this module if a module is present in step 408, and logs its serial number, part number, software version number (if any), and the status of an self-tests in step 410. Likewise, the main CPU 111 determines in step 412 whether a module is present in the third module port 114 (port C), powers on and initializes this module if present in step 414, and logs the appropriate information in step 416.

Figure 8:
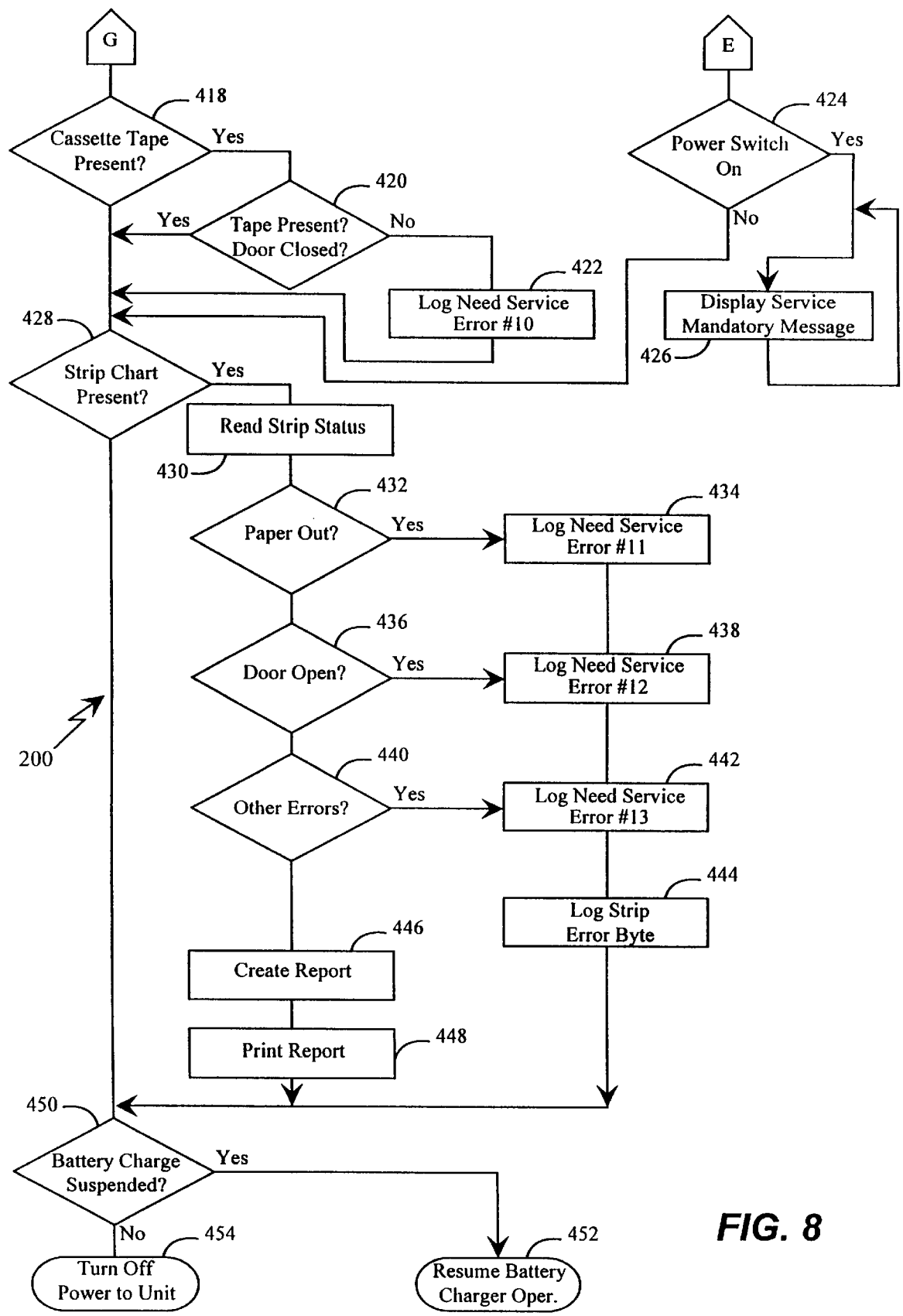

Referring now to FIG. 8, the main CPU 111 determines if the tape recorder 220 is installed within the unit 50 in step 418. If the tape recorder is present within the unit 50, then the main CPU 111 determines if a tape cassette is present within the tape recorder 220 and if the door to the tape recorder is closed in step 420. If a cassette tape is not present or if the door is open, then the main CPU 111 logs this failure as a needs service error #210 in step 422.

As noted above, as soon as the main CPU 111 determines that a service mandatory error is present, additional testing of components within the unit generally ceases. Thus, after the main CPU 111 logs one of the service mandatory errors in step 242, 248, 254, 284, 294, 306, 310, or 324, the CPU in step 424 determines if the power switch 129' is on. If the power switch 129' is on, then the main CPU 111 retrieves an appropriate service mandatory message from the CPU PROM 105 and displays this message on the display 117, by means of the display processor 116 in step 426. This service mandatory message is continually displayed while the power switch 129' is on until the power switch is turned off and unit 50 is powered down.

If the power switch 129' is off following a service mandatory error (step 424) or if the tape recorder 120 is not present within the unit 50 (step 418), the main CPU 111 in step 428 determines if the strip chart printer 122 is present. If the main CPU 111 determines that the strip chart printer 122 is present, then the CPU tests the status of the strip chart printer in step 430. If the main CPU 111 determines that the strip chart printer 122 has run out of paper in step 432, then the CPU logs this failure as a needs service error #11 in step 434.

If the strip chart printer 122 has sufficient paper, then the main CPU 111 determines if the door to the strip chart printer is open in step 436. If the main CPU 111 determines that the door to the strip chart printer 122 is open in step 436, then the CPU logs this error as a needs service error #12 in step 438. If the door is closed, then the main CPU 111 detects if the strip chart printer 122 has other errors in step 440, and logs these additional errors as a needs service error #13 in step 442.

The strip chart printer 122 is preferably the thermal strip chart printer model No. AR42 manufactured by General Scanning® of Arlington, Mass. This strip chart printer 122 contains its own self-test routines that are executed when the printer is powered up. As a result, the strip chart printer 122 is powered up in the step 430 above, and performs its own self-tests at that time. If any errors are noted by the strip chart printer 122, the main CPU 111 communicates with the strip chart printer and, if possible, causes the strip chart printer to print its own errors on the strip chart (represented as error bytes). After the main CPU 111 determines that the strip chart printer 122 is malfunctioning, then in step 444 the CPU logs these error bytes with the needs service error #13.

Figure 9:
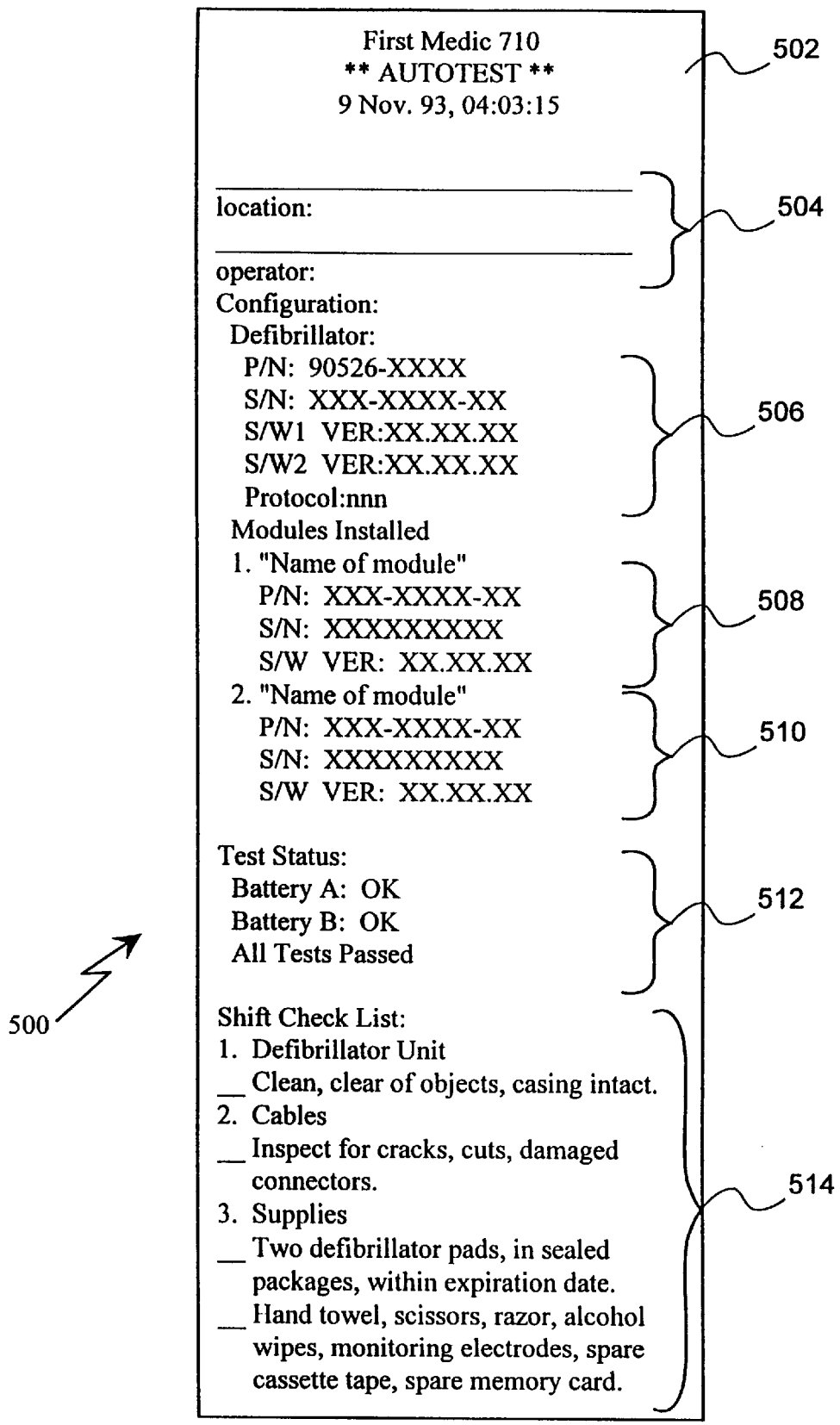
FIG. 9 is an example of a strip chart printout produced by the unit of FIGS. 1A and 1B reflecting successful completion of self-tests under the method of FIGS. 4–8.
Figure 10:
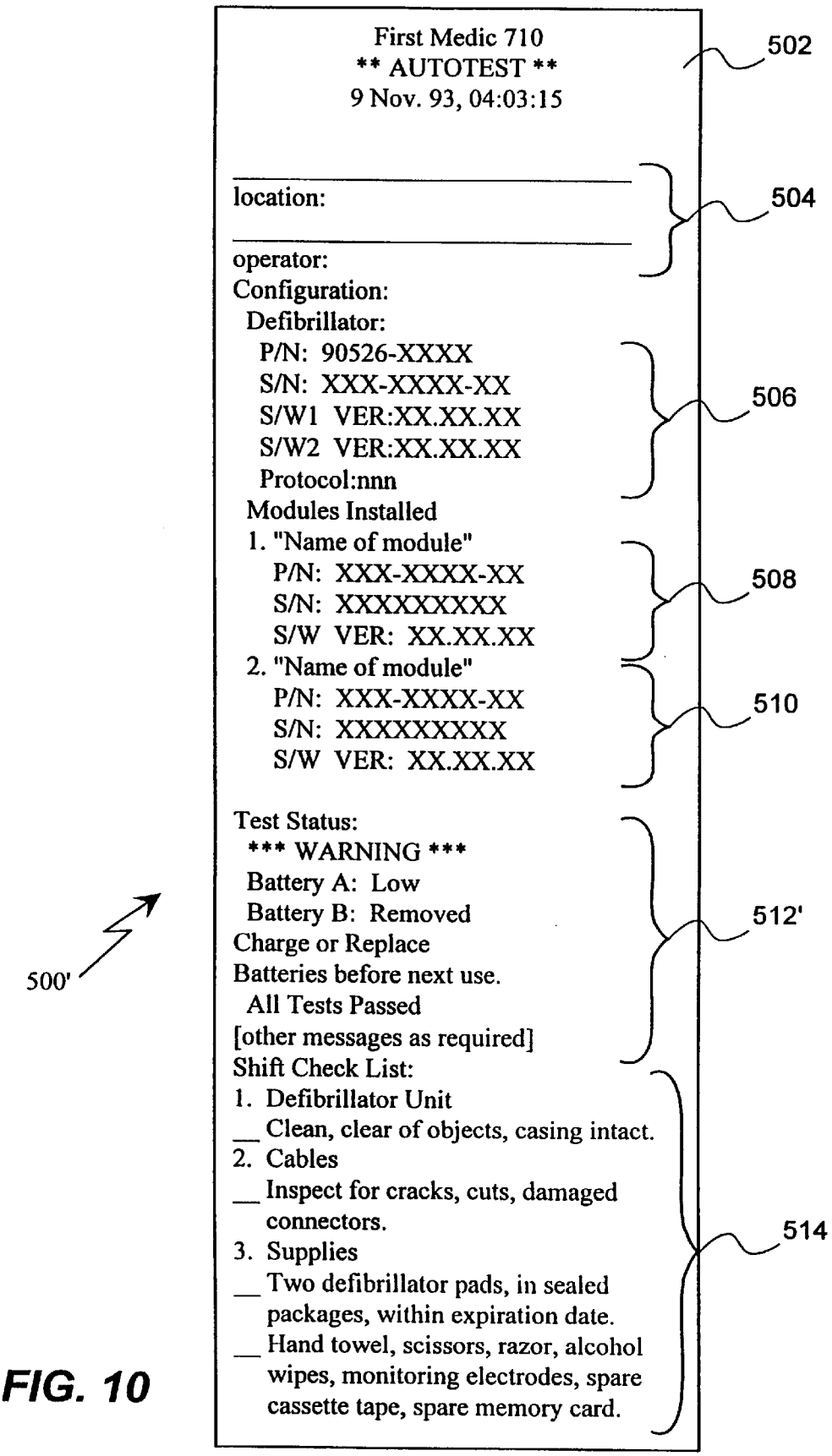
FIG. 10 is an example of a strip chart printout produced by the unit of FIGS. 1A and 1B reflecting unsuccessful completion of self-tests under the method of FIGS. 4–8.

If the strip chart printer 122 is functioning properly, then the main CPU 111 causes the strip chart printer to create a strip chart report in step 446 and print the report in step 448. FIGS. 9 and 10 show examples of strip charts 500 and 500' printed by the strip chart printer 122 in response to successful completion and failure of the tests in the autotest routine 200, all respectively. As shown in FIG. 9, the strip chart 500 begins by providing the time and date of the autotest on line 502. On lines 504, spaces are provided to allow the operator to report his or her name and the location of unit 50 on the strip chart 500 so as to keep a proper record of the particular unit's testing. On lines 506, the strip chart 500 provides the part number, serial number, software versions and protocols for the unit 50. On lines 508 and 510, the strip chart 500 provides the part numbers, serial numbers, and software version numbers for modules 1 and 2 which have been installed in the module ports 114 of the unit 50. On lines 512, the strip chart 500 provides the remainder of the result of the autotest routine 200. In this case, lines 512 indicate that the unit 50 has passes all tests of the autotest routine 200 and that the status of batteries A and B are okay. The strip chart 500 also provides a shift checklist on lines 514 modeled on the American Heart Association recommended shift checklist for defibrillator units.

The strip chart 500' is substantially similar to the strip chart 500, except that the results of the autotest routine 200 indicate that the unit 50 has some malfunctions. As shown in lines 512', for example, the battery A is low (i.e., below the needs service threshold and the battery B is removed. The strip chart 500' on lines 512' also instruct the operator to change or replace the batteries before the next use of the unit 50. Other appropriate messages would be printed thereafter to indicate the particular errors logged during the autotest routine 200. A summary of the service mandatory and needs service errors are presented in Table 1 below. Table 1 also lists the tests which failed and thereby produced the error, and in parentheses, some of the components which could be malfunctioning as a result of the failed test.

TABLE 1

Summary Of Errors Identified By Autotest Routine

| Error # | Service Mandatory Error | Needs Service Error |
|---|---|---|
| 1 | Failure of CPU self-test (main CPU 111) | Failure of EEPROM test (CPU memory 105) |
| 2 | Failure of PROM and flash PROM test (CPU memory 105) | Failure of speech record SRAM test (SRAM 121) |
| 3 | Failure of safety processor self-test or communication between safety processor and CPU (safety processor 112, main CPU 111) | Battery voltage below needs service threshold voltage (batteries A and B) |
| 4 | Failure of CPU SRAM test (CPU memory 105) | Unacceptable battery voltage drop during charging of defibrillator capacitor 103 (batteries A and B) |
| 5 | Failure of display video SRAM tests (display video SRAM 118) | Failure of real-time clock test (real-time clock 113) |
| 6 | Failure of A/D converter test (A/D converter 115, charging circuit 106) | Failure of data card slot test (data card slot 123) |
| 7 | Voltage on batteries below service mandatory threshold (batteries A and B) | Memory card not present (memory card 124) |
| 8 | Failure of transfer relay tests (transfer relay circuit 100) | Memory card nearly full (memory card 124) |
| 9 | Unacceptable voltage on defibrillator capacitor (defibrillator capacitor 103, charging circuit 106) | Failure of program voltage generator test (program voltage generator 128) |
| 10 | Failure of defibrillator capacitor decay voltage test (defibrillator capacitor 103) | Cassette tape not present or tape door not closed (tape recorder 120) |
| 11 | Failure of reference voltage test for A/D converter (front end A/D converter 133) | paper out for strip chart printer (strip chart printer 122) |
| 12 | Failure of ground voltage test for A/D converter (front end A/D converter 133) | Door open on strip chart printer (strip chart printer 122) |
| 13 | Failure of ECG preamplifier circuit test for 0 volt input (ECG preamplifier circuit 102) | Failure of strip chart printer self-test (strip chart printer 122) |
| 14 | Failure of two lead impedance circuit test for 0 volt input (two lead impedance circuit 101) | |
| 15 | Failure of two lead ECG preamplifier to peak voltage test (ECG preamplifier circuit 102) | |
| 16 | Failure of decay time test (ECG preamplifier circuit 102) | |
| 17 | Failure of two lead impedance circuit to 93-ohm impedance test (two lead impedance circuit 101) | |
| 18 | Time-out during charging of defibrillator capacitor (charging circuit 106, energy select 109, safety processor 112, main CPU 111) | |

The strip chart printouts can includes the failed tests that correspond to the error #s.

After the strip chart has been printed in step 448, or if the strip chart printer is absent or malfunctioning, the main CPU 111 in step 450 determines if charging of batteries A and B was suspended earlier in step 234. If so, then the battery charging operation is resumed in step 252. Otherwise, the main CPU 111 provides a signal to the power control circuit 129, turning the power to the unit 50 off in step 454.

Referring back to FIG. 4, after the autotest routine 200 has been performed by the unit 50, and the unit is powered back up in step 222 (i.e., the main CPU 111 determines upon power-up that the power switch 129' is on), the CPU determines in step 456 if any errors have been logged. If any errors have been logged, these errors are displayed in step 458 on the display 117. The main CPU 111 provides appropriate signals to the display processor 116, allowing the display 117 to provide feedback to the operator of the particular errors logged during the autotest routine 200. Sample messages displayed on the display 117 can include not only the error numbers noted above, but also error messages similar to those noted in Table 1.

If the error is not a service mandatory error, then the operator is prompted to acknowledge the message by pressing one of the switches 127. The unit 50 will not enter into a normal mode of operation until the operator acknowledges the logged error by depressing one of the switches 127 in step 460. If the error is service mandatory, such as to impair the essential functions of the unit 50, then the unit 50 will not allow further operation of itself until the error is corrected.

If no errors have been logged in step 456, or after the operator acknowledges a needs service error in step 460, the unit 50 begins its normal mode by performing standard normal mode self-tests in step 462. After successful completion of the normal mode self-test, the unit 50 begins its normal operation in step 464.

The unit 50 may provide an annotation of the logged test results in the memory card 124 it the memory card is present. Additionally, the unit 50 may provide feedback to the operator that a service mandatory error has been encountered by having the main CPU 111 provide an appropriate signal to the beeper 108 such that the beeper provides a continuous audible tone at selected intervals (e.g., once every 15 minutes). thereby continually notifying the operator that the autotest routine 200 has detected a service mandatory condition in the unit. If the unit 50 includes the modem card 125, the results of the autotest routine 200 can be reported to a remote location by the modem card. Furthermore, the speech enunciator circuitry 110 may provide audible error messages, including audible messages similar to those shown in Table 1 above.

The autotest routine 200 does not perform tests on the following circuits because malfunctions of these components are obvious to a trained operator; the LCD display 117, the input switches 127, the beeper 108, and the speech enunciation circuits 110. The components not tested by the autotest routine 200 are indicated by a "" in FIGS. 1A and 1B. Additionally, while the tape recorder 120, the strip chart printer 122, the display processor 116, the temperature sensor 130, and the speech record processor 119, the module ports 114, the data card slots 123, and the power control circuitry 129 are not fully tested, most malfunctions in these components are detectable through the normal use of the unit 50**, and except for the power control circuitry, do not affect the unit's essential functions.

As noted above, the unit 50 preferably a defibrillator or other piece of emergency equipment. As a result, the unit 50 must be available to provide its essential function at all times. Consequently, the autotest routine 200 halts operation whenever the operator depresses the power on switch 129' to power-up the unit 50. While not explicitly shown in the figures, the main CPU 111 recognizes an interrupt to the autotest routine 200 whenever the power on switch 129' is depressed during execution of the autotest routine. After the main CPU 111 recognizes that the power on switch 129' has been depressed and the autotest routine 200 is aborted, the CPU performs steps 456–464 described above to display any logged errors, to perform normal mode self-tests, and to resume normal mode operation.

The autotest routine 200 described herein tests the components of the unit 50 in a roughly hierarchical structure so that the more critical components of the unit are tested first, such as the CPU memory 105, A/D converter 115, battery power supply, and transfer relay circuit 100. As a result, if the unit 50 was powered up by the operator during the autotest routine 200, the more critical components of the unit will likely have already been tested and any malfunctioning of these components could be reported to the operator at this time. Some less critical components are tested toward the start of the autotest routine 200 for reasons of processing efficiency (e.g., tests of the display video and speech record SRAM 118 and 121, respectively).

The various tests performed under the autotest routine 200 are transparent to the operator in that no visible messages are displayed or sounds produced during execution of the autotest routine. Generally, all tests performed herein, with the exception of tests of the memory circuits, are preferably tested to be within a tolerance to thus allow for minor testing deviations.

The autotest system of the present invention, including the autotest routine 200, provides for a portable emergency electronic unit 50 that conducts time-consuming yet thorough tests of the components in the unit 50. The autotest system is initiated during quiescent periods of the portable emergency electronic unit 50 and immediately discontinues any testing if the unit is powered up by an operator for use in an emergency situation, thus allowing the unit to be always readily available for use.

To determine if the unit 50 is in a quiescent mode, the main CPU 111, upon power up, determines whether it was powered up by the operator (step 222), by the battery charging functions of the unit (step 232) or by the autotest start time equaling the real time from the real-time clock 113 (step 224). The autotest start time is preferably selected for a time when the unit 50 is likely in a quiescent mode. While the main CPU 111 initiates the autotest routine 200 when the autotest start time equals the real time (step 224), as described above, the battery charging functions are likely executed during a quiescent period. Therefore, the main CPU 111 can initiate the autotest routine 200 during or after the unit 50 executes the battery charging functions.

After the autotest routine completes its extensive battery of tests, the system provides the operator with a strip chart printout of the results of the autotest routine 200, a visual display of any malfunctions on the visual display 117, and the other feedback, including audible beeps from the beeper 108 or voice instructions from the speech enunciator 110. If the autotest routine 200 detects at least one of the needs service errors, the operator must acknowledge the error after powering up the unit 50. If the autotest routine 200 detects at least one of the service mandatory errors, then the unit 50 will discontinues its normal mode of operations until the operator repairs the malfunctioning component(s).

Although specific embodiments of the invention have been described for purposes of illustration, various modifications may be made without departing from the spirit and scope of the invention as will be recognized by those skilled in the relevant art based upon the detailed description provided herein. For example, while the autotest routine 200 is described as testing the various components of a defibrillator, the routine may be readily modified based on the description provided herein to test components in various other complex electronic devices. Accordingly, the invention is not limited by the disclosure, but instead its scope is to be determined entirely by reference to the following claims.

We claim:

1. A method of testing a preamplifier and an analog-to-digital converter in a front end circuit of a portable defibrillator, the method comprising the steps of:

(a) generating a test signal;

(b) applying the test signal to an input of the front end circuit, the test signal being amplified by the preamplifier in the front end circuit and digitized by the analog-to-digital converter to generate a conditioned test signal;

(c) monitoring the conditioned test signal from an output of the front end circuit; and (d) analyzing the conditioned test signal to determine a frequency response and a gain of the front end circuit.

2. The method of claim 1, wherein the conditioned test signal is analyzed to determine a high frequency response of the front end circuit and a low frequency response of the front end circuit.

3. The method of claim 2, wherein the test signal comprises a transition from a low signal state to a high signal state.

4. The method of claim 3, wherein the amplitude of the conditioned test signal is analyzed to determine the gain of the front end circuit.

5. The method of claim 3, wherein the slope of a leading edge of the conditioned test signal is analyzed to determine the high frequency response of the front end circuit.

6. The method of claim 3, wherein the test signal further comprises a transition from the high signal state back to a low signal state.

7. The method of claim 6, wherein the slope of a trailing edge of the conditioned test signal is analyzed to determine the low frequency response of the front end circuit.

8. The method of claim 1, further comprising the step of testing the operation of the analog-to-digital converter prior to applying the test signal to the input of the front end circuit by:

(a) applying a known reference voltage to the input of the analog-to-digital converter;

(b) monitoring an output value of the analog-to-digital converter; and (c) comparing the output value of the analog-to-digital converter with an expected output value, the analog-to-digital converter operating correctly if the output value is within a range surrounding the expected output value.

9. The method of claim 8, wherein the known reference voltage is ground.

10. The method of claim 8, wherein the known reference voltage is 2.5 volts.

11. An external defibrillator comprising:

(a) a high voltage delivery system comprising a defibrillator capacitor and a switch connecting the defibrillator capacitor to the error of the defibrillator;

(b) a controller operably connected to the high voltage delivery system; and (c) a self-test system coupled to the high voltage delivery system and the controller, the self-test system automatically testing the high voltage delivery system during a period when the external defibrillator has not been powered on by an operator in order to determine whether the high voltage delivery system is operating correctly, the self-test system generating a status signal to indicate to an operator of the external defibrillator if the high voltage delivery system is determined to be operating incorrectly.

12. The external defibrillator of claim 11, further comprising a clock coupled to the self-test system, the self-test system automatically testing the high voltage delivery system after an elapsed time from a previous test.

13. The external defibrillator of claim 11, further comprising a front end circuit coupled to the controller and the self-test system.

14. The external defibrillator of claim 13, wherein the self-test system automatically tests the front end circuit during a period when the external defibrillator has not been powered on by an operator in order to determine whether the front end circuit is operating correctly, the self-test system generating a status signal to indicate to an operator of the external defibrillator if the front end circuit is determined to be operating incorrectly.

15. The external defibrillator of claim 14, further comprising a battery and a charging circuit coupled to the high voltage delivery system, the controller, and the self-test system.

16. The external defibrillator of claim 15, wherein the self-test system automatically tests the battery and charging circuit during a period when the external defibrillator has not been powered on by an operator in order to determine whether the battery and charging circuit is operating correctly, the self-test system generating a status signal to indicate to an operator of the external defibrillator if the battery and charging circuit is determined to be operating incorrectly.

17. The external defibrillator of claim 11, wherein the testing performed by the self-test system is halted if the operator powers on the external defibrillator during the course of the testing.

18. The external defibrillator of claim 11, wherein the status signal is an audible alarm.

19. The external defibrillator of claim 11, wherein the status signal is a visual alarm.

20. An external defibrillator comprising:

(a) a high voltage delivery system; and (b) a self test system coupled to the high voltage delivery system, the self-test system automatically testing the high voltage delivery system during a period when the external defibrillator is in a quiescent state and generating a status signal to indicate if an error in operation of the high voltage delivery system is detected.

21. The external defibrillator of claim 20, wherein the self test system provides a visual indicator to an operator to indicate if an error is detected.

22. The external defibrillator of claim 20, wherein the self test system provides an audible indicator to an operator to indicate if an error is detected.

23. The external defibrillator of claim 20, further comprising an ECG circuit and wherein the self test system automatically tests the ECG circuit during a period when the external defibrillator is in a quiescent state.

24. The external defibrillator of claim 23, wherein the self test system tests the ECG circuit by providing a known signal into the ECG circuit and measuring a response.

25. The external defibrillator of claim 20, further comprising an impedance circuit and wherein the self test system automatically tests the impedance circuit during a period when the external defibrillator is in a quiescent state and generates a signal to indicate if an error in operation of the impedance circuit is detected.

26. The external defibrillator of claim 20, wherein the high voltage delivery system includes a battery and wherein the self test system tests the condition of the battery.

27. The external defibrillator of claim 20, wherein the high voltage delivery system includes a charging circuit and wherein the self test system tests the charging circuit by having the charging circuit produce a test pulse and measuring the output of the high voltage delivery system in response to the test pulse.

28. The external defibrillator of claim 20, wherein the high voltage delivery system includes a transfer relay circuit and wherein the self test system tests the operation of the transfer relay circuit.

29. The external defibrillator of claim 20, wherein the defibrillator further comprises a clock and wherein the self test system automatically tests the high voltage delivery system in response to an output from the clock.

30. An external defibrillator comprising:

(a) a high voltage delivery system including a capacitor and a transfer relay for providing a high voltage charge to a patient to which the external defibrillator is connected, and (b) a self test system coupled to the high voltage delivery system, the self test system automatically testing the high voltage delivery system by providing a test pulse to the high voltage delivery system in order to test the high voltage delivery system, including the transfer relay and capacitor, during a period when the external defibrillator is a quiescent state and generating a status signal to indicate if an error in the operation of the high voltage delivery system is detected.

* * * * *

UNITED STATES PATENT AND TRADEMARK OFFICE
CERTIFICATE OF CORRECTION

PATENT NO.   : 6,073,085
DATED        : June 6, 2000
INVENTOR(S)  : R.A. Wiley et al.

It is certified that error appears in the above-identified patent and that said Letters Patent is hereby corrected as shown below:

Title page, item [57],
Abstract,
Line 18, "autorest" should read -- autotest --
Line 19, "autorest" should read -- autotest --

Column 21,
Line 24 (Claim 11, line 4,), "error" should read -- exterior --

Column 22,
Line 24 (Claim 30, line 12), insert -- in-- after "is"

Signed and Sealed this

Twenty-third Day of October, 2001

Attest:

*Nicholas P. Godici*

NICHOLAS P. GODICI
*Attesting Officer*   *Acting Director of the United States Patent and Trademark Office*